United States Patent
Kobayashi et al.

(10) Patent No.: US 6,518,302 B1
(45) Date of Patent: Feb. 11, 2003

(54) REMEDIES

(75) Inventors: Eiji Kobayashi, Otsu (JP); Tuo-Ping Li, Otsu (JP); Tatsuji Enoki, Otsu (JP); Takanari Tominaga, Otsu (JP); Hiroaki Sagawa, Kusatsu (JP); Ikunoshin Kato, Uji (JP)

(73) Assignee: Takara Shuzo Co., Ltd., Kyoto (JP)

(*) Notice: Subject to any disclaimer, the term of this patent is extended or adjusted under 35 U.S.C. 154(b) by 0 days.

(21) Appl. No.: 09/889,728

(22) PCT Filed: Jan. 18, 2000

(86) PCT No.: PCT/JP00/00185

§ 371 (c)(1),
(2), (4) Date: Jul. 20, 2001

(87) PCT Pub. No.: WO00/43407

PCT Pub. Date: Jul. 27, 2000

(30) Foreign Application Priority Data

Jan. 20, 1999 (JP) .......... 11-011641
Sep. 21, 1999 (JP) .......... 11-267111

(51) Int. Cl.$^7$ .......... A01N 43/02
(52) U.S. Cl. .......... 514/450; 514/25; 514/825; 514/866; 514/903; 536/4.1; 536/54; 536/118; 536/124; 549/363
(58) Field of Search .......... 549/363; 514/450, 514/25, 825, 866, 903; 536/4.1, 54, 118, 124

(56) References Cited

U.S. PATENT DOCUMENTS 6,121,253 A 9/2000 Han et al. .......... 514/102
6,140,518 A 10/2000 Gallagher et al. .......... 552/506

FOREIGN PATENT DOCUMENTS

EP 0237992 A2 9/1987
EP 0795560 A1 9/1997
EP 1 038 879 9/2000
JP 6-80565 3/1994
JP 8092303 4/1996
WO WO 98/35704 8/1998
WO WO 99/53930 10/1999

OTHER PUBLICATIONS

Hosain et al., "Targeted Delivery of Antineoplastic Agent to Bone: Biodistribution Studies of Technetium–99m–Labeled Gem–Bisphosphonate Conjugate of Methotrexate", The Journal of Nuclear Medicine, vol. 37, No. 1, Jan. 1996.

Reinholz et al., "Distinct Mechanisms of Bisphosphonate Action Between Osteoblasts and Breast Cancer Cells: Identity of a Potent New Bisphosphonate Analoque", Breast Cancer Research and Treatment 71:257–268, 2002.

*Primary Examiner*—Alan L. Rotman
*Assistant Examiner*—Raymond Covington
(74) *Attorney, Agent, or Firm*—Browdy and Neimark

(57) ABSTRACT

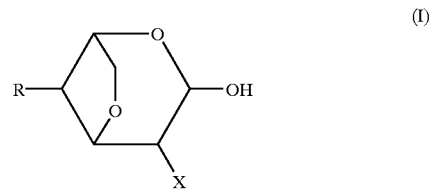

Compounds represented by general formula (I) wherein X represents OH or OSO$_3$H; and R represents a substituent other than OH which allows, after leaving, the induction of unsaturated bonds into the 3- and 4-positions of 3,6-anhydrogalactose or its sulfated derivative, and/or a substituent showing a tissue-specific affinity.

9 Claims, 27 Drawing Sheets

Chemical Shift Value (ppm)

REMEDIES

REFERENCE TO RELATED APPLICATIONS

The present application is the national stage under 35 U.S.C. §371 of international application PCT/JP00/00185, filed Jan. 18, 2000 which designated the United States, and which application was not published in the English language.

TECHNICAL FIELD

The present invention relates to a therapeutic agent. More specifically, the present invention relates to a physiologically active substance which is useful in a field of medicine and to the use of the substance.

BACKGROUND ART

Recently, attention has drawn to a mode of death of cells or tissues which is called as apoptosis (self-blasting or self-destruction of cells).

The apoptosis is a death that has been originally programmed in the genome of a cell, and is different from necrosis, which is a pathological cell death. Specifically, it is considered that the following processes lead to the death. The activation of a gene that programs the apoptosis triggered by certain external or internal factor(s) causes the biosynthesis of a protein of programming cell death. In some cases, a protein of programming cell death that exists in a cell in its inactive form becomes activated. The thus generated active protein of programming cell death destroys the cell.

Induction of the apoptosis in desired tissues or cells is very worthwhile because it makes it possible to eliminate unnecessary or harmful cells from a living body in a natural manner.

OBJECTS OF INVENTION

The main object of the present invention is to provide a substance having a physiological function such as an apoptosis-inducing activity which is useful in a field of medicine, and the use of the substance.

SUMMARY OF INVENTION

The present invention is outlined as follows. The first aspect of the present invention relates to a compound of general formula I:

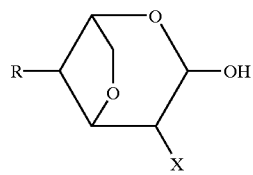

(I)

wherein X is OH or $OSO_3H$, R is a substituent other than OH, the substituent being a substituent of which the elimination enables introduction of unsaturated bonds at 3-position and 4-position of 3,6-anhydrogalactose or a sulfated derivative thereof and/or a substituent having a tissue-specific affinity.

The second aspect of the present invention relates to a pharmaceutical composition containing the compound of general formula I as an active ingredient for treating or preventing a disease sensitive to the compound of general formula I.

The third aspect of the present invention relates to a food or a drink which contains, which is produced by diluting, and/or which is produced by adding thereto the compound of general formula I.

BRIEF DESCRIPTION OF DRAWINGS

FIG. 15 illustrates the $NO_2^-$ concentration in a culture medium obtained by culturing with the addition of compound (9).

DETAILED DESCRIPTION OF THE INVENTION

Figure 1:
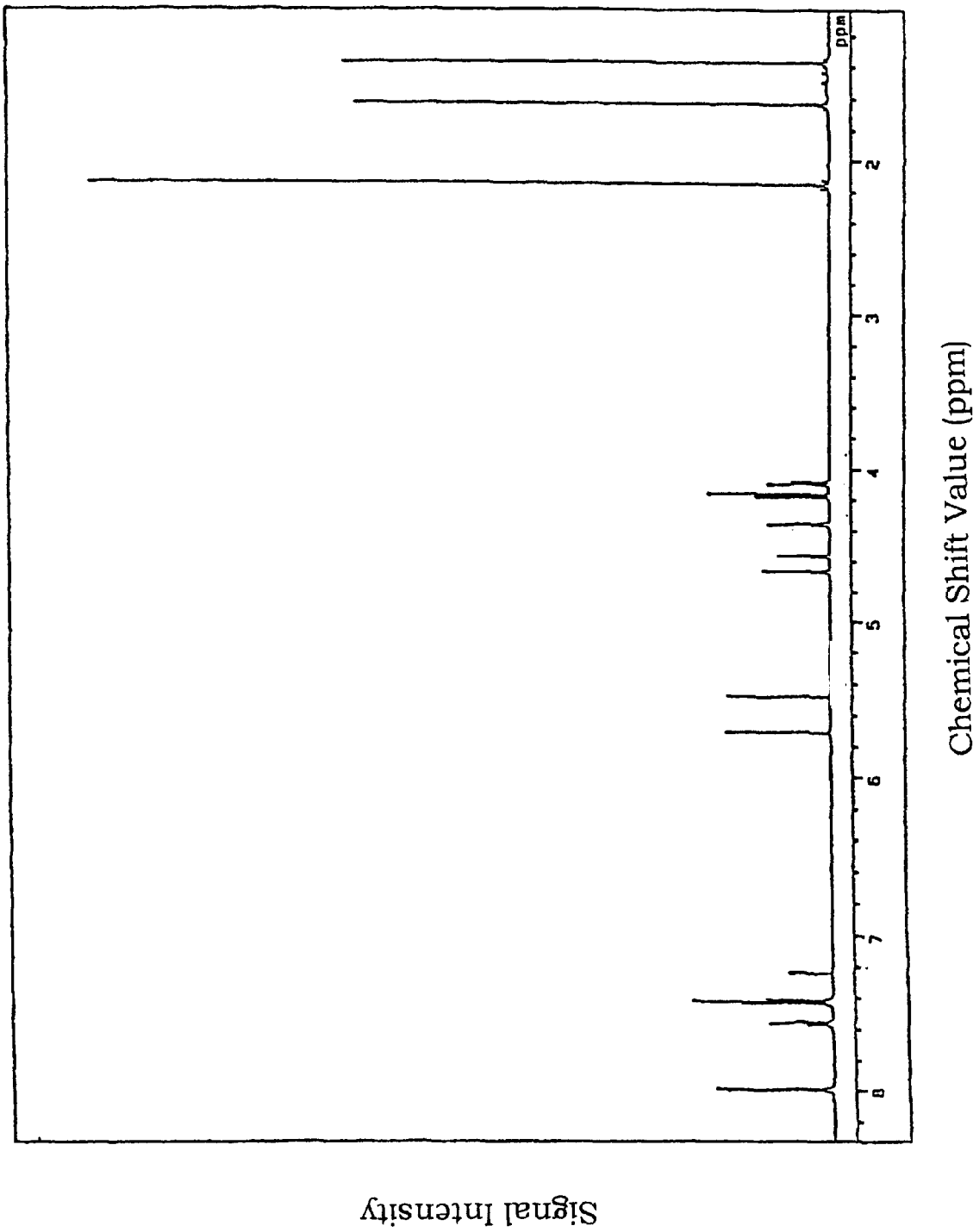
FIG. 1 illustrates the $^1$H-NMR spectrum of compound (8).

The present invention will be explained in detail.

According to the present invention, a method for producing the compound of general formula I is not specifically limited. For example, the compound can be obtained according to a known chemical synthesis method. For example, the compound of general formula I can be obtained by introducing a substituent of arbitrary (R) to a hydroxyl group at 4-position of 3,6-anhydrogalactose or a sulfated derivative thereof as described in Examples below.

As used herein, the compound of general formula I means the compound of general formula I, an aldehyde thereof of general formula II or a hydrate thereof of general formula III. The structures of the compounds represented by general formulas I to III may be represented by using different expression forms. It is intended that the compounds of general formulas I to III include compounds represented by such different expression forms and their possible tautomers. In addition, the configurations of general formulas I to III are not limited to specific ones as long as desired activities are exerted. The D-form or L-form, or a mixture thereof may be used.

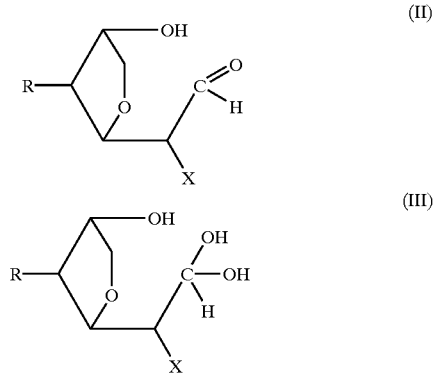

The representative compound of the present invention, the compound of general formula I, has 3,6-anhydrogalactose or a sulfated derivative thereof at its reducing end and has R attached at 4-position of 3,6-anhydrogalactose or the sulfated derivative thereof. In this compound, 3,6-anhydrogalactos or the sulfated derivative thereof at the reducing end is altered under physiological conditions into, for example, a compound of general formula IV:

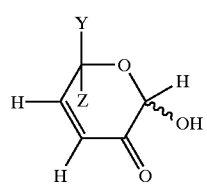

wherein Y and Z are H or $CH_2OH$, provided that when Z is $CH_2OH$, Y is H and when Z is H, Y is —$CH_2OH$.

The compound of general formula IV resulted from the alteration has a physiological activity such as an apoptosis-inducing activity, a carcinostatic activity, an activity of inhibiting active oxygen production, an activity of inhibiting nitrogen monoxide production, an activity of inhibiting α-glycosidase, an activity of inhibiting interleukin production, an activity of inducing heme oxygenase production or an immunoregulatory activity in a physiological environment.

According to the present invention, R is a substituent other than OH. For example, it can serve as a leaving group in a reaction that generates a compound of general formula IV to introduce unsaturated bonds at 3-position and 4-position of 3,6-anhydrogalactose or a sulfated derivative thereof and/or has a tissue-specific affinity. Examples of R include saturated hydrocarbons, unsaturated hydrocarbons, aromatic hydrocarbons, saccharides, sugar chains, nucleic acids, lipids, peptides, proteins, glycoproteins, glycolipids and phospholipids.

The mode of the bond between R and 4-position of 3,6-anhydrogalactose or a sulfated derivative thereof is not limited to specific one. For example, the bond is cleaved in a reaction that generates a compound of general formula IV and exemplified by an ester bond and an ether bond.

By using a specific substituent having an affinity to a tissue for R, it is possible to specifically localize the compound of general formula I to a specific site (tissue, cell, organ, etc.). The compound of general formula IV can be generated as a result of the elimination of the substituent at the site, thereby exerting a physiological activity at the specific site of interest. Furthermore, the period of time and the level of exertion can be controlled.

Furthermore, it is possible to increase the absorbability of the compound of general formula I into a living body by using a specific substituent for R. Specifically, by using a specific substituent as R, it is possible to allow the compound of general formula IV to exert its physiological activity only at a selected local site in which it is concentrated after efficient absorption into a living body instead of exerting the activity immediately after administration.

Thus, the present invention provides a prodrug for generating the compound of general formula IV in vivo, which prodrug contains the compound of general formula I as an active ingredient.

The prodrug can be formulated by using the compound of general formula I as its active ingredient, and formulating it with a known pharmaceutical carrier according to a conventional method. The composition is generally mixed with a pharmaceutically acceptable liquid or solid carrier and, optionally, solvent, dispersing agent, emulsifier, buffering agent, stabilizer, excipient, binder, disintegrant, lubricant and the like to formulate it. The formulation may be in a form of a solid preparation such as tablet, granule, powder, epipastic and capsule, or a liquid preparation such as normal solution, suspension and emulsion. In addition, it may be formulated into a dried preparation, which can be reconstituted as a liquid preparation by adding an appropriate carrier before use.

The prodrug can be administrated as either an oral preparation or a parenteral preparation such as injectable preparation and drips.

The pharmaceutical carrier can be selected according to the above-mentioned particular administration route and dosage form. For an oral preparation, starch, lactose, sucrose, mannit, carboxymethylcellulose, cornstarch, inorganic salts and the like are utilized, for example. Binder, disintegrant, surfactant, lubricant, fluidity-promoting agent, tasting agent, coloring agent, flavoring agent and the like can also be included in oral preparations.

A parenteral preparation can be prepared according to conventional methods by dissolving or suspending the compound of general formula I as an active ingredient of a prodrug in a diluent. The diluents include injectable distilled water, physiological saline, aqueous glucose solution, injectable vegetable oil, sesame oil, peanut oil, soybean oil, corn oil, propylene glycol and polyethylene glycol. Optionally, sterilizer, stabilizer, osmotic regulator, smoothing agent and the like may be added to the solution or suspension.

The prodrug of the present invention is administered through a suitable route for the dosage form of the composition. The administration route is not limited to a specific one. The prodrug can be administered internally or externally (or topically) or by injection. The injectable preparation can be administrated intravenously, intramuscularly, subcutaneously, intradermally and the like, for example. External preparations include a suppository.

A dosage of the prodrug is appropriately determined and varies depending on the particular dosage form, administration route and purpose as well as age, weight and conditions of a patient to be treated. In general, a daily dosage for an adult person is 10 µg to 200 mg/kg in terms of the amount of the active ingredient contained in the formulation. Of course, the dosage can vary depending on various factors. Therefore, in some cases, a less dosage than the above may be sufficient but, in other cases, a dosage more than the above may be required. The pharmaceutical composition of the present invention can be administrated orally as it is, or it can be taken daily by adding to selected foods and drinks.

The compounds of general formula I of the present invention have physiological activities such as an apoptosis-inducing activity, a carcinostatic activity, antioxidant activities such as an activity of inhibiting active oxygen production, an activity of inhibiting lipid peroxide radical production and an activity of inhibiting nitrogen monoxide production, an antimicrobial activity to pathogenic microorganism, an antimutagenic activity, an immunoregulatory activity, an anti-inflammatory activity, an antiallergic activity, an activity of regulating cytokine production, an antirheumatic activity, an antidiabetic activity, and an activity of inducing heme oxygenase production. Based on these activities, pharmaceutical compositions for treating or preventing the following diseases can be produced using the compound of general formula I as an active ingredient. Such diseases include a disease that requires induction of apoptosis for its treatment or prevention, a cancerous disease, a disease that requires inhibition of active oxygen production for its treatment or prevention, a disease that requires inhibition of lipid peroxide radical production for its treatment or prevention, a disease that requires inhibition of nitrogen monoxide production for its treatment or prevention, a disease that requires immunoregulation for its treatment or prevention, a disease that requires inhibition of inflammation for its treatment or prevention, a disease that requires inhibition of allergy for its treatment or prevention, a disease that requires regulation of cytokine production for its treatment or prevention and a disease that requires induction of heme oxygenase production for its treatment or prevention. In other words, the following pharmaceutical compositions for treating or preventing diseases sensitive to the compound can be produced: a composition for inducing apoptosis, a carcinostatic composition, antioxidant compositions such as a composition for inhibiting active oxygen production, a composition for inhibiting lipid peroxide radical production and a composition for inhibiting nitrogen monoxide production, an antimicrobial composition, an antiviral composition, an antimutagenic composition, an anti-hyperglycemic composition, an anti-hyperlipidemic composition, an immunoregulatory composition, an anti-inflammatory composition, an antiallergic composition, a composition for regulating cytokine production, an antirheumatic composition, an antidiabetic composition, and a composition for inducing heme oxygenase production.

The composition for inducing apoptosis of the present invention, which contains the compound of general formula I as an active ingredient, is effective in eliminating autoreactive lymphocytes from patients with autoimmune diseases, tumor cells, cells infected with a virus and the like. It can be used to eliminate unnecessary or harmful cells from a living body in a natural manner by inducing apoptosis in desired tissues or cells. Examples of diseases for which the composition for inducing apoptosis of the present invention is effective include autoimmune diseases such as systemic lupus erythematosus, immune-mediated glomerulonephritis, multiple sclerosis and collagen disease, and rheumatism.

The composition for inducing apoptosis of the present invention can be used in a method for inducing apoptosis. The method is useful for elucidating the mechanism of induction of apoptosis, as well as screening for inducers of apoptosis and inhibitors of apoptosis induction.

The compound of general formula I used in the present invention is useful for inhibition of production of oxidizing substances such as active oxygen. Therefore, an antioxidant composition such as a composition for inhibiting active oxygen production that contains the compound as its active ingredient is useful for treating or preventing diseases caused by production and/or excess of active oxygen.

Active oxygen can be generally classified into radical active oxygen and non-radical active oxygen. The radical active oxygen includes hydroxy radical, hydroxyperoxy radical, peroxy radical, alkoxy radical, nitrogen dioxide, nitric monoxide (hereinafter referred to as NO), thylradical and superoxide. On the other hand, the non-radical active oxygen includes singlet oxygen, hydrogen peroxide, lipid hydroperoxide, hypochlorous acid, ozone and peroxonitrite. All of them are involved in a number of pathological states such as various inflammatory diseases, diabetes, cancers, arteriosclerosis, neurological diseases and ischemic re-perfusion disorder.

Active oxygen is always produced at a low concentration through several pathways in a living body. The thus produced active oxygen is inevitable and includes the following: superoxide and hydrogen peroxide physiologically leaking out from an electron transport system such as that in mitochondria, hydroxy radical whose production is catalyzed by a transition metal such as copper and iron, hypochlorous acid generated by neutrophils or monocytes for defense against infections and NO produced by decomposition of arginine. A living body has a system for eliminating active oxygen including enzymes and small molecule compounds against the production of the active oxygen to maintain the balance between the production and the elimination. However, the living body is oxidatively damaged if the production system becomes predominant over the elimination system due to the activation of the production system for some reasons or, to the contrary, due to the inactivation of the elimination system. Such conditions are called as oxidative stress.

Furthermore, in addition to the internal imbalance, the living body is always exposed to oxidative stress due to external materials such as atmosphere and foods. Therefore, the oxidative stress is inevitable in everyone's daily life.

In other words, a living body is always exposed to circumstances which lead to the diseases caused by or worsening of the disease conditions due to oxidative stress, which is involved in various diseases as described above. Therefore, the antioxidant composition such as the composition for inhibiting active oxygen production of the present invention is also useful for preventing and treating the diseases caused by the oxidative stress or preventing the worsening of the disease conditions due to the oxidative stress.

A lipid peroxidation reaction is always associated with the oxidative stress. The reaction proceeds once a lipid peroxide radical is produced. 4-hydroxy-2-nonenal (HNE) produced in the reaction is a toxic aldehyde that specifically targets glutathione or proteins. The products of the reactions between HNE and proteins are detected in various disease tissues and considered to be inducers of disease conditions associated with oxidative stress. Accordingly, the antioxidant composition containing the antioxidant substance used in the present invention (i.e., the compound of general formula I), which can inhibit production of lipid peroxide radicals, as an active ingredient is useful for preventing and treating age-related diseases caused by oxidative stress.

NO is the essential component of endothelium-derived relaxing factor (EDRF) [Nature, 327:524–526 (1987)]. The present invention provides a pharmaceutical composition for treating or preventing a disease that requires inhibition of NO production for its treatment or prevention.

Examples of diseases that require inhibition of NO production for their treatment or prevention according to the present invention include, but are not limited to, systemic hypotension caused by toxic shock, treatment with certain cytokines and the like, reduction in blood pressure response, diabetes, vascular dysfunction, angiectasis caused by diseases, tissue injury, cardiovascular ischemia, hyperalgesia, cerebral ischemia, diseases accompanying vascularization, cancers and the like.

Vascularization is necessary for the growth of a solid cancer. Vascular endothelial growth factor/vascular permeability factor (VEGF) plays important roles in this process. NO induces VEGF in various tumor cells. The composition for inhibiting NO production of the present invention also inhibits VEGF production in tumor cells by inhibiting NO production, thereby inhibiting vascularization around cancer tissues. When the composition for inhibiting NO production of the present invention is administered to a mouse in which tumor cells have been transplanted subcutaneously to form solid cancers, vascularization around the cancer tissue becomes insufficient and the cancer falls out.

Nitrosoamines are a series of compounds in which nitrso group is attached to a secondary amine. Many of the several hundred types of nitrosoamines known in the art exhibit carcinogenic activity on animals by damaging their DNA. Nitrosoamines are considered to have a profound relation to carcinogenesis in humans. Nitrosoamine is usually produced by a reaction between a nitrite and an amine in a stomach. NO produces a nitrosoamine by reaction with an amine even under physiological conditions at neutral pH. NO production is increased in patients with clonorchiasis or cirrhosis, which epidemiologically have high relationship with cancers. Therefore, carcinogenesis of a high-risk group, in particular, can be prevented by administrating the composition for inhibiting NO production of the present invention to prevent the increase in NO production. As described above, the composition for inhibiting NO production of the present invention exhibits its carcinostatic activity in two steps, that is, suppression of carcinogenesis and inhibition of vascularization in cancerous tissues.

NO also induces edema, which is characteristically observed in inflammatory lesion. In other words, it increases vascular permeability [Maeda et al., Japanese Journal of Cancer Research, 85:331–334 (1994)]. NO increases biosynthesis of prostaglandins which are inflammatory mediators [Salvemini et al., Proceedings of National Academy of Sciences, USA, 90:7240–7244 (1993)]. On the other hand, NO rapidly reacts with superoxide radical to produce peroxonitrite ion. This peroxonitrite ion is considered to cause inflammatory damages in cells and tissues.

NO production is induced when activated immune cells enter into an organ and release cytokines. Insulin-dependent diabetes is caused by specific destruction of islet β cells, which destruction is considered to be caused by NO. Synovial fluid in the lesion of a patient with rheumatoid arthritis, osteoarthrosis, gouty arthritis or arthritis associated with Behçet's disease contains NO at a concentration higher than that in the normal joint of the same patient or joints of a healthy individual. When the composition for inhibiting NO production of the present invention is administered to such a patient, NO production in the lesion is inhibited, resulting in the improvement of disease conditions.

NO production is increased during cerebral ischemia and after re-perfusion, resulting in damages in cerebral tissues. Administration of the composition for inhibiting NO production of the present invention to a patient during cerebral ischemia relieves the damages in cerebral tissues and improves the prognosis.

Arachidonic acid metabolism is greatly involved in the rise of inflammation and dolor in tissues. Arachidonic acid derived from phospholipid in cell membrane is metabolized in vivo into three substances, prostaglandin, prostacyclin and thromboxane, by the action of cyclooxygenase. Among these, prostaglandin has an angiectatic activity and, consequently, an activity of increasing bloodstream to organs. In particular, prostaglandins $E_2$ and $I_2$ increase edemas and leukocyte infiltration at inflammation sites due to their activity of increasing bloodstream. The compound of general formula I of the present invention has an activity of inhibiting prostaglandin $E_2$ synthesis. Thus, the pharmaceutical composition containing the compound of general formula I of the present invention as an active ingredient is useful for the treatment or prevention of a disease that requires inhibition of prostaglandin $E_2$ synthesis for its treatment or prevention. Sedative and anti-inflammatory activities can be exerted by administering the composition for inhibiting prostaglandin $E_2$ synthesis of the present invention to inhibit the biosynthesis of prostaglandin. Furthermore, leukocytes infiltrated into inflammation sites produce active oxygen and cause oxidative stress conditions. Accordingly, the composition for inhibiting prostaglandin $E_2$ synthesis of the present invention which inhibits the biosynthesis of prostaglandin is also useful for the prevention, treatment or prevention of worsening of various diseases caused by oxidative stress as described above.

In addition, NO induces edema which is characteristically observed in inflammatory lesions, i.e., increases vascular permeability, and increases biosynthesis of prostaglandins which are inflammatory mediators as described above. The effect of inhibiting NO production and the effect of inhibiting prostaglandin $E_2$ synthesis of the present invention act synergistically to exhibit sedative and anti-inflammatory activities as well as synergistic effects in the prevention, treatment or prevention of worsening of various diseases caused by oxidative stress According to the present invention, cytokines are exemplified by interleukins. Interleukin is a generic name of proteinous biologically active substances produced by lymphocytes, monocytes and the like. Existence of interleukins 1 to 18 is currently known. Interleukins are exemplified by IL-6 and IL-10.

A cDNA for IL-6 was first cloned as one encoding a differentiation factor that induces the terminal differentiation of B cells. IL-6 is involved not only in immune response but also differentiation of cells in hematopoietic system and nerve system as well as acute phase response. It is also closely related to onset of various immunological abnormalities and inflammatory diseases as well as lymphoid tumors. IL-6 induces antibody production in B cells to produce IgM, IgG and IgA classes of immunoglobulins, but is not involved in class switching unlike IL-4. IL-6 acts as a growth factor for B cells and plasmacytes. In addition, it participates with T cells. Specifically, IL-6 allows T cells to grow or differentiate. IL-6 also participates in hematopoietic system. It, in cooperation with IL-3, allows hematopoietic stem cells to grow by shortening G0 phase. It promotes maturation of megakaryocytes to induce increase in platelets. IL-6 is also involved in acute phase reaction which is an immediate reaction of a living body to infection with a bacterium or a virus, or malignant tumor. IL-6 also participates with nerve system. It is secreted from cells in nerve system such as glioblastomas and astrocytomas and acts to induce differentiation of nerve system. In case of rheumatoid arthritis and systemic lupus erythematosus, activation of B cells is observed and IL-6 is present in synovial fluid in a patient at a high concentration. In case of Castleman syndrome which is characterized by systemic lymphadenopathy, the concentration of IL-6 in blood is very high. A large amount of IL-6 is produced from tumor cells in a patient with atrial myxoma having autoimmune disease-like symptoms. Furthermore, since the growth of myeloma cells derived from a patient with multiple myeloma is inhibited using an anti-IL-6 antibody, it is highly possible that IL-6 serves as a self growth factor for myeloma cells. IL-6 is contained in urine from a patient with primary glomerulonephritis and acts as a growth factor for renal mesangial cells [Kohei Miyazono and Kazuo Sugamura (eds.), "Bio Science Yogo Library: Cytokine—Growth Factor", pp. 28–29, Yodo-sha (1995)]. It is possible to treat or prevent the conditions of such diseases, which are considered to be caused by abnormal production of IL-6, by administering the compound used in the present invention to inhibit IL-6 production.

Examples of diseases that require inhibition of IL-10 production for their treatment or prevention include a disease that is accompanied by lowered immunity. The compound of the present invention is useful for such a disease.

Two isozymes of heme oxygenase (HO), HO-1 (33 kDa) and HO-2 (36 kDa), are known. HO-2 has a structure in which an extra amino acid sequence consisting of 20 amino acid residues is added at the N-terminus of HO-1. Although the remaining portions share a homology of 40 to 50%, the high-order structures are very similar each other. Both of them have hydrophobic regions at the C-termini. They are attached to microsome membranes at these portions. Since a soluble fraction having a heme-degrading activity is obtained by treating microsome with trypsin, it is considered that the large domain including the active center protrudes on the cytoplasmic side.

HO-1 is an inducible enzyme. It is remarkably induced in various cells by chemical and physical factors such as heme (the substrate), heavy metal ions, certain organic compounds, hydrogen peroxide, heat shock, UV irradiation and ischemia. HO-2 is a constitutive enzyme. It is expressed in various tissues. In particular, the activity is high in brain and testis. HO degrades heme into biliverdin, CO and iron.

Biliverdin is further converted into bilirubin by the action of a reductase. Bilirubin has the following activities as an antioxidant: an antioxidant activity for fatty acid, an activity of scavenging lipid radical, an activity of inhibiting production of hydroperoxides of phospholipids, neutral fat and cholesterol due to oxygen radicals generated in large quantities upon phagocytosis by neutrophils, an activity of inhibiting production of low density lipoprotein (LDL) which is closely related to onset of arteriosclerosis, and an activity of scavenging singlet oxygen. Thus, bilirubin plays an important role in a living body as an endogenous antioxidant. Various radicals act on various biological substances including proteins and nucleic acids in addition to lipids as factors that cause chronic diseases and cancer. Bilirubin reduces the various radicals (Porphyrin Kenkyu-kai (ed.) "Porphyrin/Heme no seimeikagaku: idenbyo, gan, kogaku oyo nado he no tenkai" Tokyo Kagaku Dozin (1995)). Thus, it is possible to induce production of bilirubin, which has an antioxidant activity, by inducing HO to treat or prevent diseases due to various radicals. The compound used in the present invention induces HO production and is useful for treating or preventing diseases that require induction of HO production for their treatment or prevention as described above.

The immunoregulatory composition containing the compound of general formula I as an active ingredient has immunoregulatory activities such as an activity of inhibiting lymphocyte blastogenesis and an activity of inhibiting mixed lymphocyte reaction. Thus, the immunoregulatory composition is useful as a pharmaceutical composition for treating or preventing diseases due to abnormality of the immune systems or immune factors.

Lymphocyte blastogenesis is a reaction in which mitogen binds to a receptor on the surface of a lymphocyte to activate the lymphocyte and promotes its division and proliferation. Mixed lymphocyte reaction is a reaction in which lymphocytes obtained from allogenic animals are mixed together and cultured, thereby inducing activation of lymphocytes due to incompatibility of major histocompatibility antigens to promote the division and proliferation of lymphocytes. The immunoregulatory composition of the present invention inhibits these reactions and is particularly useful for treating and preventing chronic diseases caused by abnormal increase in lymphocytes, including autoimmune diseases such as chronic nephritis, chronic colitis, type I diabetes and rheumatoid arthritis. The composition is also useful for suppression of graft rejection.

The composition for inducing apoptosis of the present invention can be formulated by using the compound of general formula I as its active ingredient, and formulating it with a known pharmaceutical carrier. The composition for inducing apoptosis is produced according to the same manner as that as described above with respect to the production of the prodrug.

The composition for inducing apoptosis is administered through a suitable route for the dosage form of the composition. The administration route is not limited to a specific one. The composition can be administered internally or externally (or topically) or by injection. The injectable preparation can be administrated intravenously, intramuscularly, subcutaneously, intradermally and the like, for example. External preparations include a suppository.

A dosage of the composition for inducing apoptosis is appropriately determined and varies depending on the particular dosage form, administration route and purpose as well as age, weight and conditions of a patient to be treated. In general, a daily dosage for an adult person is $10 \mu g$ to $200$ mg/kg in terms of the amount of the active ingredient contained in the formulation. Of course, the dosage can vary depending on various factors. Therefore, in some cases, a less dosage than the above may be sufficient but, in other cases, a dosage more than the above may be required. The pharmaceutical composition of the present invention can be administrated orally as it is, or it can be taken daily by adding to selected foods and drinks.

The carcinostatic composition of the present invention can be formulated by using the compound of general formula I as its active ingredient, and formulating it with a known pharmaceutical carrier. The carcinostatic composition is produced according to the same manner as that as described above with respect to the production of the prodrug.

The carcinostatic composition is administered through a suitable route for the dosage form of the composition. The administration route is not limited to a specific one. The composition can be administered internally or externally (or topically) or by injection. The injectable preparation can be administrated intravenously, intramuscularly, subcutaneously, intradermally and the like, for example. External preparations include a suppository.

A dosage of the carcinostatic composition is appropriately determined and varies depending on the particular dosage form, administration route and purpose as well as age, weight and conditions of a patient to be treated. In general, a daily dosage for an adult person is 10 $\mu$g to 200 mg/kg in terms of the amount of the active ingredient contained in the formulation. Of course, the dosage can vary depending on various factors. Therefore, in some cases, a less dosage than the above may be sufficient but, in other cases, a dosage more than the above may be required. The pharmaceutical composition of the present invention can be administrated orally as it is, or it can be taken daily by adding to selected foods and drinks.

The antioxidant composition, the composition for inhibiting active oxygen production, the composition for inhibiting lipid peroxide radical production and the composition for inhibiting NO production containing the compound of general formula I as their active ingredients are produced according to the same manner as that as described above with respect to the production of the composition for inducing apoptosis. The dose and the method of use depend on the condition. They are used according to the same manner as described above with respect to the composition for inducing apoptosis.

The antioxidant composition, the composition for inhibiting active oxygen production, the composition for inhibiting lipid peroxide radical production or the composition for inhibiting NO production is administered through a suitable route for the dosage form of the composition. The administration route is not limited to a specific one. The composition can be administered internally or externally (or topically) or by injection. The injectable preparation can be administrated intravenously, intramuscularly, subcutaneously, intradermally and the like, for example. External preparations include a suppository.

A dosage of the antioxidant composition, the composition for inhibiting active oxygen production, the composition for inhibiting lipid peroxide radical production or the composition for inhibiting NO production is appropriately determined and varies depending on the particular dosage form, administration route and purpose as well as age, weight and conditions of a patient to be treated. In general, a daily dosage for an adult person is 10 $\mu$g to 200 mg/kg in terms of the amount of the active ingredient contained in the formulation. Of course, the dosage can vary depending on various factors. Therefore, in some cases, a less dosage than the above may be sufficient but, in other cases, a dosage more than the above may be required. The pharmaceutical composition of the present invention can be administrated orally as it is, or it can be taken daily by adding to selected foods and drinks.

Furthermore, the compound of general formula I is converted into the compound of general formula IV in vivo to exhibit an activity of inhibiting an $\alpha$-glycosidase such as sucrase. Thus, an anti-hyperglycemic composition, an anti-hyperlipidemic composition, an anti-obese composition, an antidiabetic composition and the like containing the compound of general formula I as their active ingredients can be produced. Such pharmaceutical compositions can be produced according to the same manner as that as described above with respect to the production of the composition for inducing apoptosis. The dose and the method of use depend on the condition of the disease to be treated or prevented. They are used according to the same manner as described above with respect to the composition for inducing apoptosis.

A food or a drink which contains, which is produced by diluting, and/or which is produced by adding thereto the compound of general formula I (hereinafter referred to as the food or the drink of the present invention) is very useful for ameliorating the disease states of or preventing the diseases sensitive to the compound of general formula I such as a disease that requires induction of apoptosis for its treatment or prevention, a cancerous disease, a disease that requires inhibition of active oxygen production for its treatment or prevention, a disease that requires inhibition of NO production for its treatment or prevention, a disease caused by a pathogenic microorganism, a disease induced by a mutagen and the like based on an apoptosis-inducing activity, a carcinostatic activity, an antioxidant activity, an antimicrobial activity to pathogenic microorganism, an antimutagenic activity and the like.

The process for producing the foods or drinks of the present invention is not limited to a specific one. Any processes including cooking, processing and other generally employed processes for producing foods and drinks can be used as long as the resultant foods or drinks contain, are produced by adding thereto, and/or are produced by diluting the compound of general formula I as their active ingredients.

As long as the food or drink of the present invention contains, is produced by diluting and/or is produced by adding thereto the compound of general formula I in an amount necessary for exhibiting its physiological activity, its form is not limited to a specific one. The food or drink includes that in any edible form such as tablets, granule and capsule.

The food or the drink of the present invention contains the compound of general formula I which has a physiological activity. The physiological functions of the compound such as an apoptosis-inducing activity and a carcinostatic activity provide an effect of preventing carcinogenesis, an effect of suppressing cancers or the like upon taking the food or drink. That is, the foods or drinks of the present invention are healthy foods or drinks which have effects of ameliorating the disease states of or preventing the diseases sensitive to the compound of general formula I. Particularly, they are useful for keeping gastrointestinal health.

The compound of general formula I has antioxidant activities such as an activity of inhibiting active oxygen production and an activity of inhibiting lipid peroxide radical production. Thus, it can be used for the production of antioxidant foods or antioxidant drinks as an antioxidant for antioxidant foods or drinks such as an agent for inhibiting active oxygen production, an agent for inhibiting lipid peroxide radical production or an agent for inhibiting NO production.

In addition, the present invention provides a sweetener containing the compound of general formula I. The compound of general formula I has a sweet taste. Thus, it is useful as an active ingredient of a low-calorie sweetener as a substitute for sugar.

No acute toxicity was observed when a physiologically effective amount of the compound of general formula I was orally administered to a mouse.

EXAMPLES

The following examples further illustrate the present invention in detail but are not to be construed to limit the scope thereof.

Example 1

(1) 1,2-O-isopropylidene-3,6-anhydro-D-galactose [compound (3)]

A method as shown in equation I:

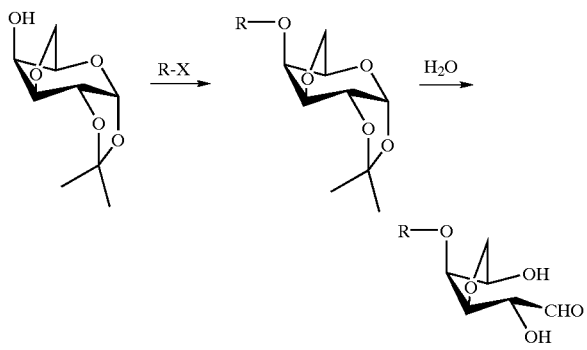

was used for specifically replacing the hydroxyl group at 4-position of 3,6-anhydrogalactose with various substituents.

Specifically, after a substituent of interest (R) was introduced to the hydroxyl group at 4-position of the compound (3), only the 1,2-O-isopropylidene group was removed under acidic conditions.

The compound (3) required for the above was synthesized by deriving 3,6-anhydro-D-galactose [compound (2)] from α-O-methyl-D-galactopyranose [compound (1)] according to the method of Haworth et al. [Imperial Collection of Science and Technology, 620–631 (1940)] as shown in equation II below and then introducing 1,2-O-isopropylidene according to the method of Hirase et al. [Bulletin of the Chemical Society of Japan, 41:626–628 (1968)].

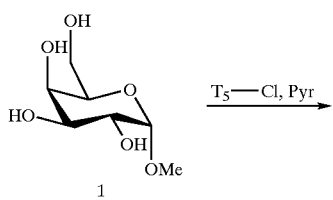

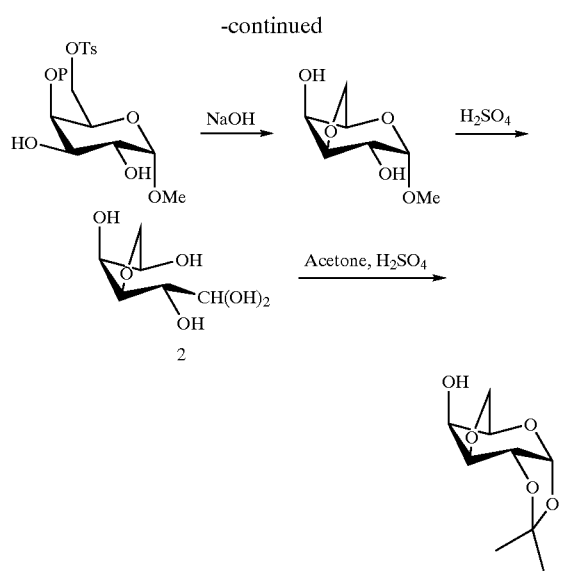

(2) Synthesis of saccharide donor

Introduction of saccharide to the compound (3) in this Example was carried out according to the trichloroacetoimidate method developed by Schmidt et al. [Liebigs ann. Chem., 1249–1256 (1983)].

Trichloroimidate derivative of saccharide was synthesized according to the method of Kobayashi et al. [Carbohydrate Research, 201:51–67 (1990)] as shown in equation III below.

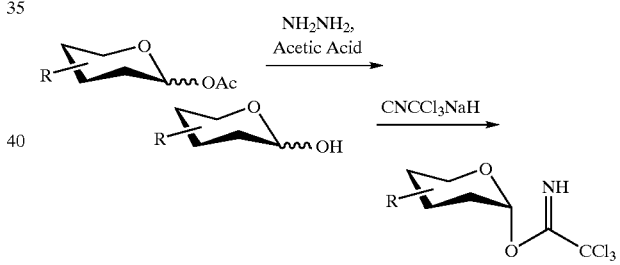

Compounds (4), (5) and (6) represented by formulas V to VII, respectively, were synthesized according to the above-mentioned method.

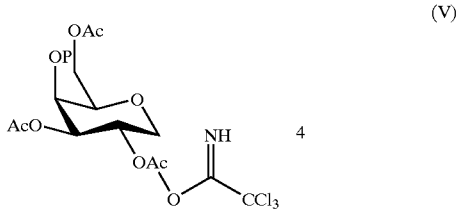

(V)

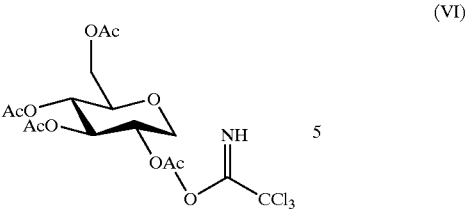

(VI)

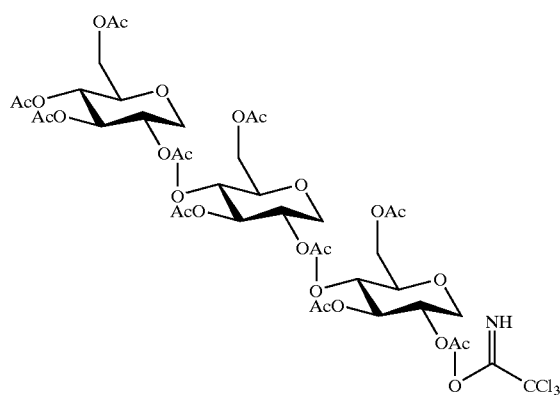

(3) 4-O-benzoyl-3,6-anhydro-D-galactose [compound (7)]

(i) 4-O-benzoyl-1,2-O-isopropylidene-3,6-anhydro-D-galactose [compound (8)]

100 mg (0.5 mmol) of the compound (3), 170 mg (0.75 mmol) of benzoic anhydride (Nacalai Tesque; Code. 042-24) and 12.2 mg of (0.1 mmol) of 4-dimethylaminopyridine (Nacalai Tesque; Code. 129-22) were dissolved in 5 ml of dichloromethane. After cooling on ice, 104 ml (0.75 mmol) of triethylamine (Nacalai Tesque; Code. 348-05) was added thereto. The mixture was stirred at room temperature for 2 hours.

The reaction mixture was concentrated and then subjected to silica gel chromatography using hexane:ethyl acetate=11:2 as a developing solvent to obtain 146 mg of compound (8). Structural analysis of the compound (8) was carried out by nuclear magnetic resonance (NMR) spectrometry (JNM-A500 (Nippon Denshi)).

$^1$H-NMR

δ 1.37(3H, s, Me), 1.64(3H, s, Me), 4.09(1H, dd, J=3.5, 16.5 Hz, H-6), 4.17(1H, d, J=10.5 Hz, H-6), 4.35(1H, dd, J=2.5, 5 Hz, H-2), 4.56(1H, m, H-5), 4.68(1H, d, J=5 Hz, H-3), 5.48(1H, d, J=2.5 Hz, H-1), 5.71(1H, d, J=1.5 Hz, H-4), 7.43(2H, t, J=8.5 Hz, Bzl), 7.59(1H, td, J=1, 8.5, Bzl), 8.00(2H, dd, J=1, 8.5, Bzl)

The sample was dissolved in heavy chloroform. The results are expressed assuming the chemical shift value of proton of chloroform as 7.24 ppm.

FIG. 1 illustrates the $^1$H-NMR spectrum of compound (8). In FIG. 1, the horizontal axis represents the chemical shift value (ppm) and the vertical axis represents the signal intensity.

(ii) Compound (7)

80 mg of the compound (8) was dissolved in 30 ml of dichloromethane. Trifluoroacetic acid/water (2.85 ml/0.15 ml) was added thereto. The mixture was stirred at room temperature for 3 hours. The reaction mixture was diluted with 300 ml of ethyl acetate and washed with saturated sodium hydrogencarbonate in water. The organic layer was concentrated under reduced pressure and subjected to silica gel chromatography using chloroform:methanol=25:1 as a developing solvent to obtain 52 mg of compound (7) of formula VIII below. The compound (7) was subjected to structural analysis by nuclear magnetic resonance (NMR) spectrometry (JNM-A500 (Nippon Denshi)) and mass spectrometry (MS) (DX302 mass spectrometer (Nippon Denshi)).

$^1$H-NMR

Figure 2:
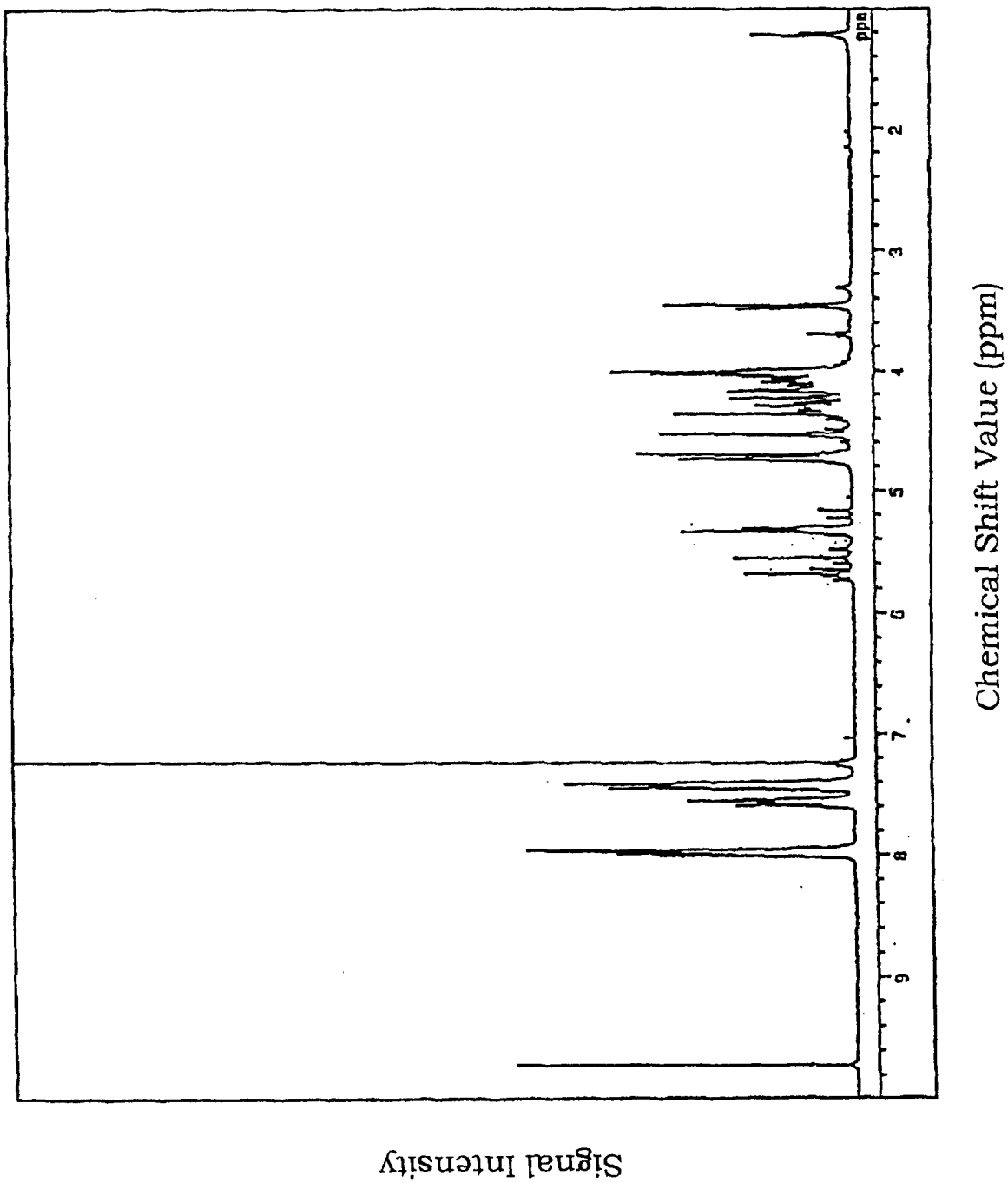
FIG. 2 illustrates the $^1$H-NMR spectrum of compound (7).

The compound (7) was dissolved in heavy chloroform. Structural analysis by nuclear magnetic resonance was carried out. FIG. 2 illustrates the $^1$H-NMR spectrum of compound (7). In FIG. 2, the horizontal axis represents the chemical shift value (ppm) and the vertical axis represents the signal intensity.

Since the aldehyde at 1-position of 3,6-anhydro-D-galactose of this substance was in an equilibrium state with hemiacetal bond (α,β) in heavy chloroform, it was impossible to identify the signals. Disappearance of signals from 1,2-O-isopropylidene of the compound (8) (signals at δ 1.37 ppm and 1.64 ppm in FIG. 1) and generation of a signal from aldehyde (signal at δ 9.75 ppm in FIG. 2) were confirmed.

FAB-MS m/z 267(M+H)$^+$ Glycerol was used for matrix.

(4) 4-O-(β-D-2,3,4,6-tetra-O-acetylgalactopyranosyl)-3,6-anhydro-D-galactose [compound (9)]

(i) 4-O-(β-D-2,3,4,6-tetra-O-acetylgalactopyranosyl)-1,2-O-isopropylidene-3,6-anhydro-D-galactose [compound (10)]

2 ml of dichloromethane was added to 355 mg (0.72 mmol) of the compound (4) and 146 mg (0.72 mmol) of the compound (3) under argon atmosphere. The mixture was cooled to −20° C. using ice/salt. 32 ml (0.14 mmol) $CF_3SO_3Si(CH_3)_3$ (Tokyo Kasei; T0871)/2 ml dichloromethane was slowly added thereto. The mixture was stirred at −20° C. for 1.5 hours. After saturated sodium hydrogencarbonate in water and ethyl acetate were added to the reaction mixture, organic layer was recovered. When this organic layer was subjected to thin-layer chromatography using hexane:ethyl acetate=1:1 as a developing solvent, a product of interest was detected at Rf value of about 0.45. The organic layer was dried over magnesium sulfate anhydrous, concentrated under reduced pressure and subjected to silica gel chromatography using hexane:ethyl acetate=5:4 as a developing solvent to obtain 101 mg of compound (10). The compound (10) was subjected to structural analysis by nuclear magnetic resonance (NMR) spectrometry (JNM-A500 (Nippon Denshi)).

$^1$H-NMR

δ 1.29(3H, s, Me), 1.51(3H, s, Me), 1.94(3H, s, Ac), 1.97(3H, s, Ac), 1.98(3H, s, Ac), 2.08(3H, s, Ac), 3.90(2H, m), 3.96(1H, d, J=10 Hz, H-6a), 4.06(1H, dd, J=6, 11 Hz, H-6b), 4.11(1H, dd, J=7, 11 Hz, H-6b), 4.23(1H, dd, J=3, 5 Hz, H-2a), 4.36(1H, d, J=5 Hz, H-3a), 4.42(1H, m, H-5a), 4.47(1H, d, J=1.5 Hz, H-4a), 4.52(1H, d, J=8 Hz, H-1b), 4.95(1H, dd, J=3.5, 10 Hz, H-3b), 5.11(1H, dd, J=8, 10 Hz, H-2b), 5.33(1H, d, J=3.5 Hz, H-4b), 5.35(1H, d, J=3.0 Hz, H-1a)

The sample was dissolved in heavy chloroform. The results are expressed assuming the chemical shift value of proton of chloroform as 7.24 ppm.

Figure 3:
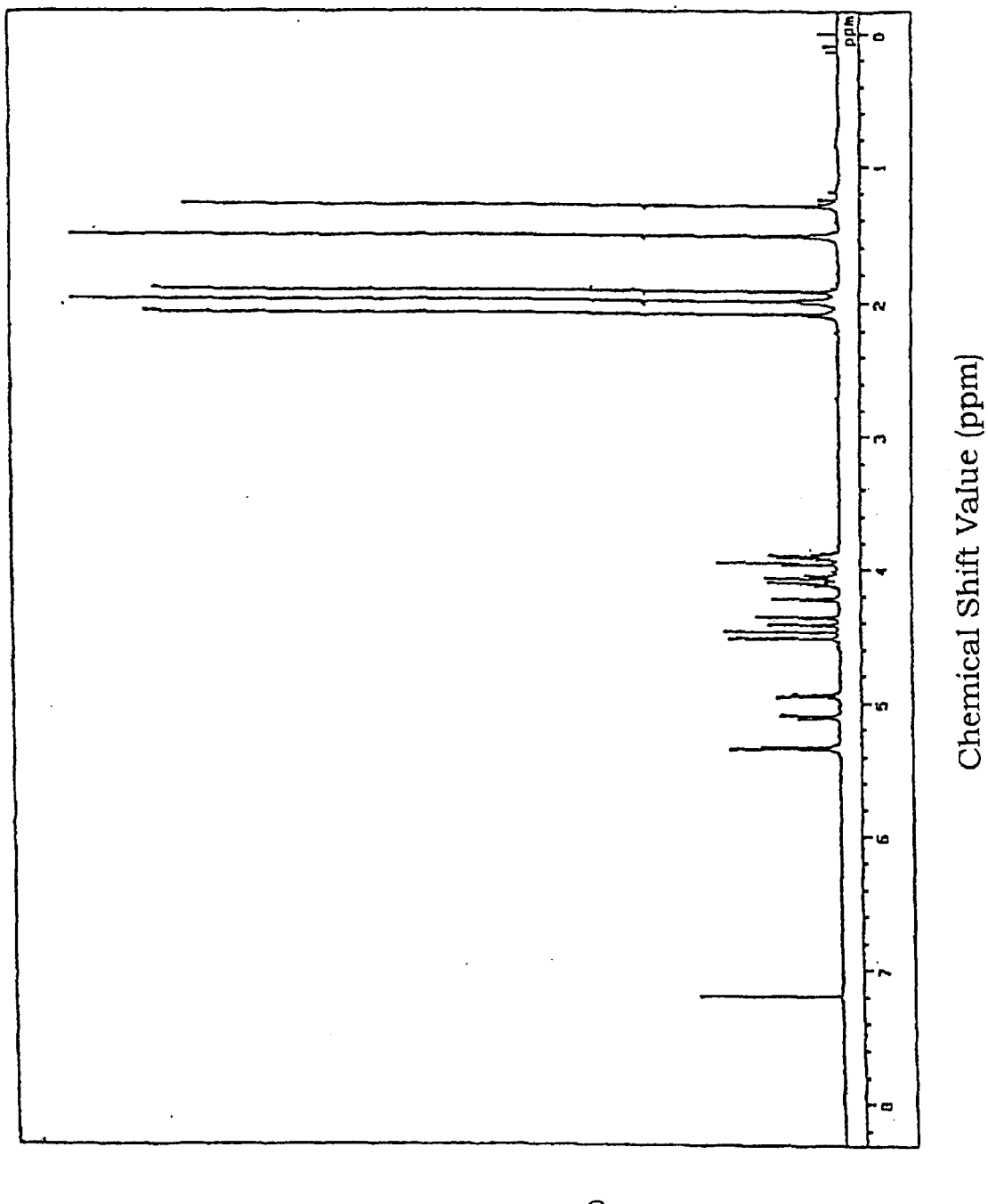
FIG. 3 illustrates the $^1$H-NMR spectrum of compound (10).

FIG. 3 illustrates the $^1$H-NMR spectrum of compound (10). In FIG. 3, the horizontal axis represents the chemical shift value (ppm) and the vertical axis represents the signal intensity.

(ii) Compound (9)

44 mg of the compound (10) was dissolved in 10 ml of dichloromethane. Trifluoroacetic acid/water (1.14 ml/60 ml) was added thereto. The mixture was stirred at room temperature for 3 hours. The reaction mixture concentrated under reduced pressure and subjected to silica gel chromatography using chloroform:methanol=19:1 as a developing solvent to obtain 9 mg of compound (9). The compound (9) was subjected to structural analysis by nuclear magnetic resonance (NMR) spectrometry (JNM-A500 (Nippon Denshi)).

$^1$H-NMR

δ 1.91(3H, s, Ac), 1.99(3H, s, Ac), 2.02(3H, s, Ac), 2.11(3H, s, Ac), 3.45(1H, dd, J=3.5, 6.5 Hz, H-2a), 3.81(1H, dd, J=3, 10 Hz, H-6a), 3.87(1H, dd, J=4.5, 10 Hz, H-6a), 3.91(1H, t, J=3.5 Hz, H-3a), 4.23(4H, m), 4.37(1H, dt, J=3, 4.5 Hz, H-5a), 4.89(1H, d, J=8 Hz, H-1b), 4.93(1H, d, J=6.5 Hz, H-1a), 5.05(1H, dd, J=8, 10 Hz, H-2b), 5.22(1H, dd, J=3, 10 Hz, H-3b), 5.35(1H, d, J=3.0 Hz, H-4b)

The sample was dissolved in heavy water. The results are expressed assuming the chemical shift value of. HOD as 4.65 ppm.

Figure 4:
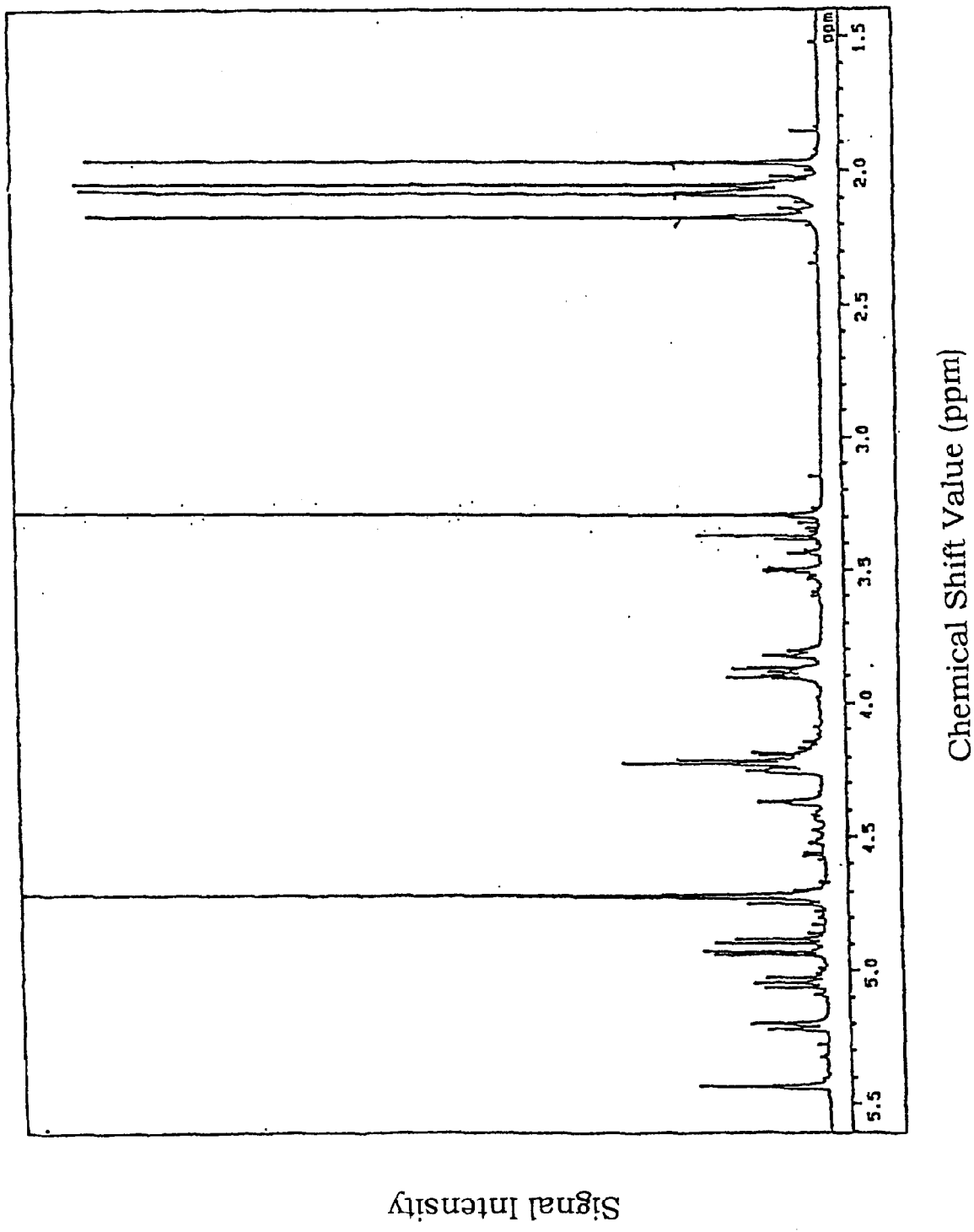
FIG. 4 illustrates the $^1$H-NMR spectrum of compound (9).

FIG. 4 illustrates the $^1$H-NMR spectrum of compound (9). In FIG. 4, the horizontal axis represents the chemical shift value (ppm) and the vertical axis represents the signal intensity.

The numbers for peak identification in $^1$H-NMR are as indicated in formula IX below.

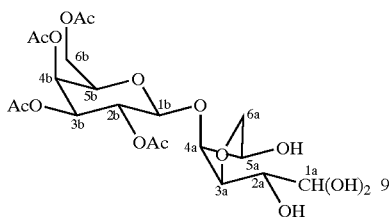

(IX)

(5) 4-O-β-D-glucopyranosyl-3,6-anhydro-D-galactose [compound (11)]

(i) 4-O-(β-D-2,3,4,6-tetra-O-acetylglucopyranosyl)-1,2-O-isopropylidene-3,6-anhydro-D-galactose [compound 12]

10 ml of dichloromethane was added to 1.22 g (2.47 mmol) of the compound (5) and 354 mg (1.75 mmol) of the compound (3) under argon atmosphere. The mixture was cooled to −20° C. using ice/salt. 100 ml (0.4 mmol) $CF_3SO_3Si(CH_3)_3$/2 ml dichloromethane was slowly added thereto. The mixture was stirred at −20° C. for 2.5 hours. After saturated sodium hydrogencarbonate in water and ethyl acetate were added to the reaction mixture, organic layer was recovered. When this organic layer was subjected to thin-layer chromatography using hexane:ethyl acetate= 1:1 as a developing solvent, a product of interest was detected at Rf value of about 0.45. The organic layer was dried over magnesium sulfate anhydrous, concentrated under reduced pressure and subjected to silica gel chromatography using hexane:ethyl acetate=5:4 as a developing solvent to obtain 230 mg of compound (12). The compound (12) was subjected to structural analysis by nuclear magnetic resonance (NMR) spectrometry (JNM-A500 (Nippon Denshi)).

$^1$H-NMR

δ 1.29(3H, s, Me), 1.51(3H, s, Me), 1.94(3H, s, Ac), 1.97(3H, s, Ac), 1.98(3H, s, Ac), 2.02(3H, s, Ac), 3.69(1H, ddd, J=2.5, 5, 10 Hz, H-5b), 3.89(1H, dd, J=3, 10 Hz, H-6a), 3.96(1H, d, J=10 Hz, H-6a), 4.09(1H, dd, J=2.5, 12.5 Hz, H-6b), 4.17(1H, dd, J=5, 12.5 Hz, H-6b), 4.22(1H, dd, J=3.5, 4.5 Hz, H-2a), 4.36(1H, d, J=4.5 Hz, H-3a), 4.43(1H, m, H-5a), 4.45(1H, d, J=1.5 Hz, H-4a), 4.57(1H, d, J=7.5 Hz, H-1b), 4.90(1H, dd, J=7.5, 10 Hz, H-2b), 4.99(1H, t, J=10 Hz, H-3b), 5.14(1H, t, J=10 Hz, H-4b), 5.34(1H, d, J=3.5 Hz, H-1a)

Figure 5:
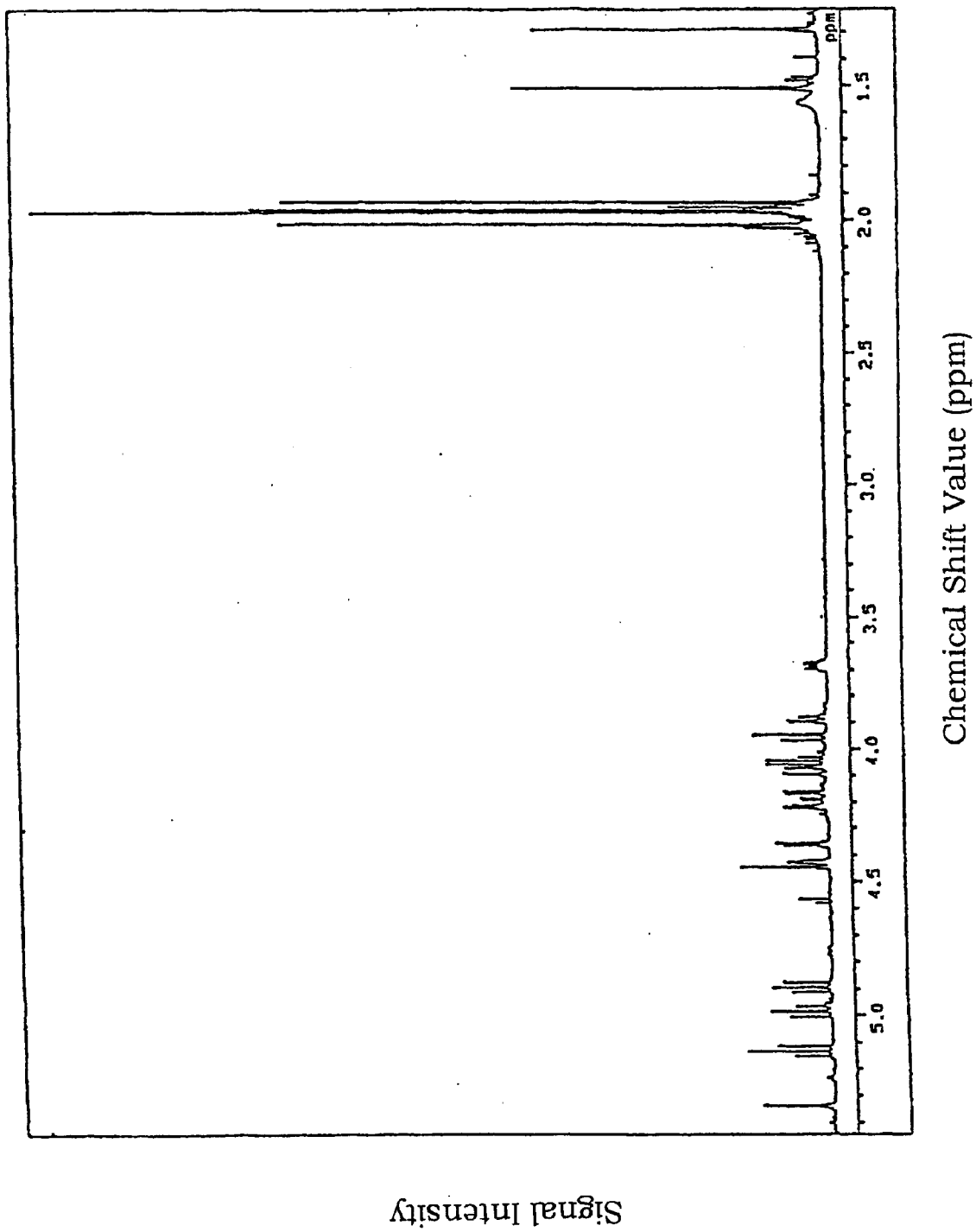
FIG. 5 illustrates the $^1$H-NMR spectrum of compound (12).

The sample was dissolved in heavy chloroform. The results are expressed assuming the chemical shift value of proton of chloroform as 7.24 ppm. FIG. 5 illustrates the $^1$H-NMR spectrum of compound (12). In FIG. 5, the horizontal axis represents the chemical shift value (ppm) and the vertical axis represents the signal intensity.

(ii) 4-O-β-D-glucopyranosyl-1,2-O-isopropylidene-3,6-anhydro-D-galactose [compound (13)]

230 mg of the compound (12) was dissolved in 5 ml of methanol. 1.5 ml of 0.1 N sodium methoxide solution in methanol was added thereto. The mixture was stirred at room temperature for 30 minutes. When this reaction mixture was subjected to thin-layer chromatography using chloroform:methanol=5:1 as a developing solvent, a product of interest was detected at Rf value of about 0.3. The reaction mixture was neutralized using carbonic acid gas, concentrated under reduced pressure and then subjected to silica gel chromatography using chloroform:methanol=5:1 as a developing solvent to obtain 90 mg of compound (13).

(iii) Compound (11)

90 mg of the compound (13) was dissolved in 4 ml of water. 2 ml of 0.1 N sulfuric acid solution was added thereto. The mixture was stirred at 95° C. for 2 hours. When this reaction mixture was subjected to thin-layer chromatography using butanol:ethanol:water=5:5:1 as a developing solvent, a product of interest was detected at Rf value of about 0.5. The reaction mixture was neutralized using barium carbonate. After removing precipitates, the aqueous solution was lyophilized to obtain 64 mg of compound (11). The compound (11) was subjected to structural analysis by nuclear magnetic resonance (NMR) spectrometry (JNM-A500 (Nippon Denshi)) and mass spectrometry (MS) (DX302 mass spectrometer (Nippon Denshi)).

$^1$H-NMR

δ 3.18(1H, dd, J=8, 9 Hz, H-2b), 3.27(1H, t, J=9 Hz, H-3b), 3.39(2H, m), 3.52(1H, dd, J=3.5, 6 Hz, H-2a), 3.60(1H, dd, J=6.5, 12.5 Hz, H-6b), 3.73(1H, dd, J=2.5, 10 Hz, H-6a), 3.82(1H, dd, J=2.5, 12.5 Hz, H-6b), 3.88(1H, dd, J=4.5, 10 Hz, H-6a), 3.95(1H, dd, J=3.5, 5 Hz, H-3a), 4.16(1H, dd, J=2.5, 5 Hz, H-4a), 4.35(1H, dt, J=2.5, 4.5 Hz, H-5a), 4.45(1H, d, J=8 Hz, H-1b), 4.89(1H, d, J=6 Hz, H-1a)

Figure 6:
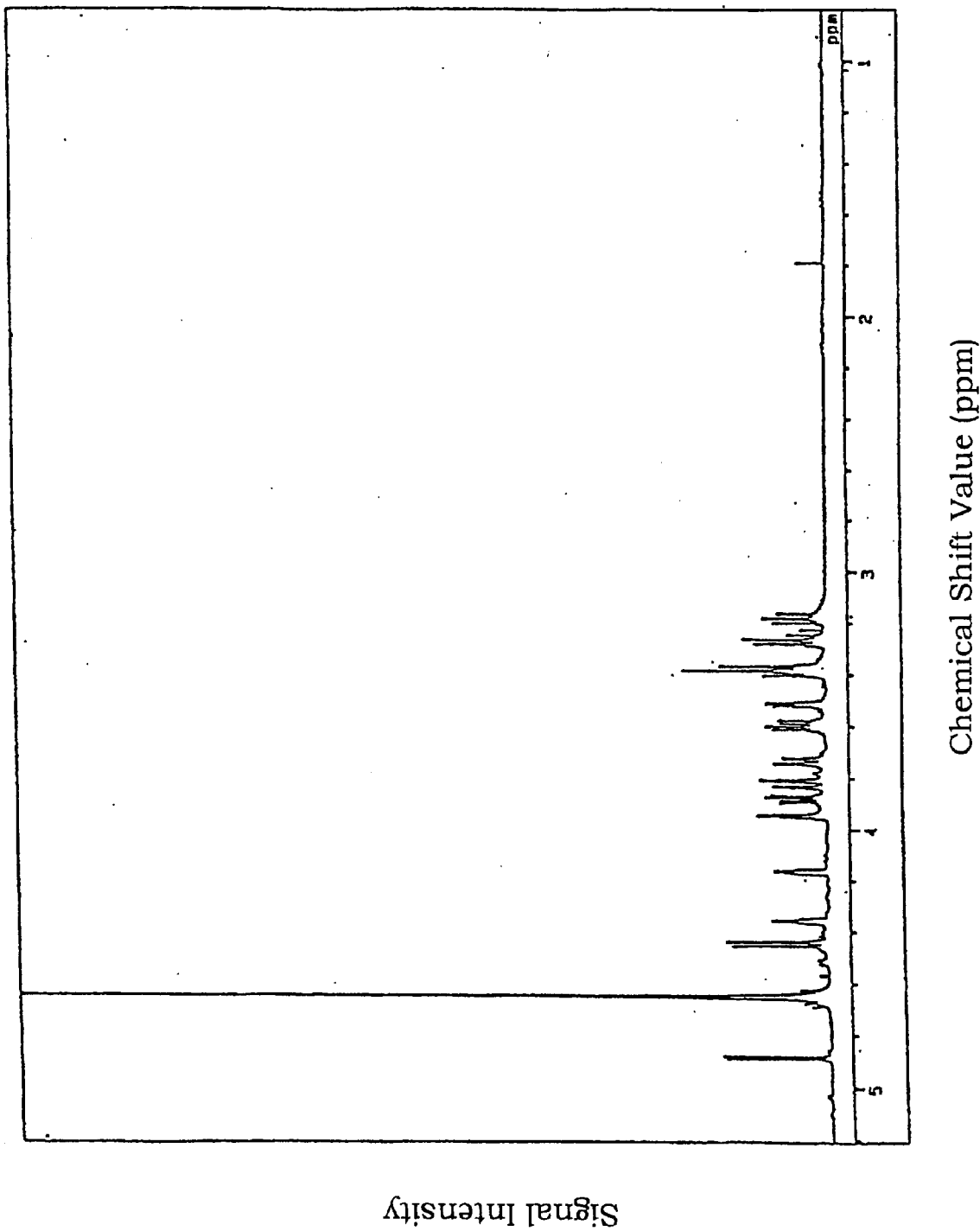
FIG. 6 illustrates the $^1$H-NMR spectrum of compound (11).

The sample was dissolved in heavy water. The results are expressed assuming the chemical shift value of HOD as 4.65 ppm. FIG. 6 illustrates the $^1$H-NMR spectrum of compound (11). In FIG. 6, the horizontal axis represents the chemical shift value (ppm) and the vertical axis represents the signal intensity.

The peak identification in $^1$H-NMR is as indicated in formula X below.

(X)

FAB-MS m/z 325(M+H)$^+$ Glycerol was used for matrix.

(6) 4-O-β-maltotoriosyl-3,6-anhydro-D-galactose [compound (14)]

(1) 4-O-(dodeca-O-acetylmaltotoriosyl)-1,2-O-isopropylidene-3,6-anhydro-D-galactose [compound (15)]

30 ml of dichloromethane was added to 5.1 g (4.75 mmol) of the compound (6) and 960 mg (4.75 mmol) of the compound (3) under argon atmosphere. The mixture was cooled to −20° C. using ice/salt. 200 ml (0.95 mmol) $CF_3SO_3Si(CH_3)_3$/2 ml dichloromethane was slowly added thereto. The mixture was stirred at −20° C. for 1.5 hours. After saturated sodium hydrogencarbonate in water and ethyl acetate were added to the reaction mixture, organic layer was: recovered. When this organic layer was subjected to thin-layer chromatography using hexane:ethyl acetate= 1:2 as a developing solvent, a product of interest was detected at Rf value of about 0.4. The organic layer was dried over magnesium sulfate anhydrous, concentrated under reduced pressure and subjected to silica gel chromatography using hexane ethyl acetate=2:1 as a developing solvent to obtain 936 mg of compound (15).

(ii) 1,2-O-isopropylidene-4-O-maltotoriosyl-3,6-anhydro-D-galactose [compound (16)]

936 mg of the compound (15) was dissolved in 45 ml of methanol. 4.5 ml of 0.1 N sodium methoxide solution in methanol was added thereto. The mixture was stirred at room temperature for 1 hour. When this reaction mixture was subjected to thin-layer chromatography using chloroform:methanol=1:1 as a developing solvent, a product of interest was detected at Rf value of about 0.5. The reaction mixture was neutralized using carbonic acid gas, concentrated under reduced pressure and then subjected to silica gel chromatography using chloroform:methanol=1:1 as a developing solvent to obtain 457 mg of compound (16).

(iii) Compound (14)

457 mg of the compound (16) was dissolved in 15 ml of 0.02 N sulfuric acid solution. The mixture was stirred at 95° C. for 2 hours. When this reaction mixture was subjected to thin-layer chromatography using butanol ethanol:water= 5:5:1 as a developing solvent, a product of interest was detected at Rf value of about 0.5. The reaction mixture was neutralized using barium carbonate. After removing precipitates, the aqueous solution was lyophilized to obtain 390 mg of compound (14).

The compound (14) was subjected to structural analysis by nuclear magnetic resonance (NMR) spectrometry (JNM-A500 (Nippon Denshi)) and mass spectrometry (MS) (DX302 mass spectrometer (Nippon Denshi)).

$^1$H-NMR

δ 3.22(1H, dd, J=8, 9.5 Hz, H-2b), 3.30(1H, t, J=9.5 Hz, H-3b), 3.46(1H, dd, J=4, 10 Hz, H-2c), 3.50(1H, dd, J=4, 10 Hz, H-2d), 3.5–3.75(14H, m), 3.83(3H, m), 3.88(1H, dd, J=5, 10.5 Hz, H-6a), 3.94(1H, dd, J=2.5, 5 Hz, H-4a), 4.16(1H, dd, J=2.5, 5 Hz, H-5a), 4.46(1H, d, J=8 Hz, H-1b), 4.46(1H, d, J=6.5 Hz, H-1a), 5.27(2H, d, J=4 Hz, H-1d, 1c)

Figure 7:
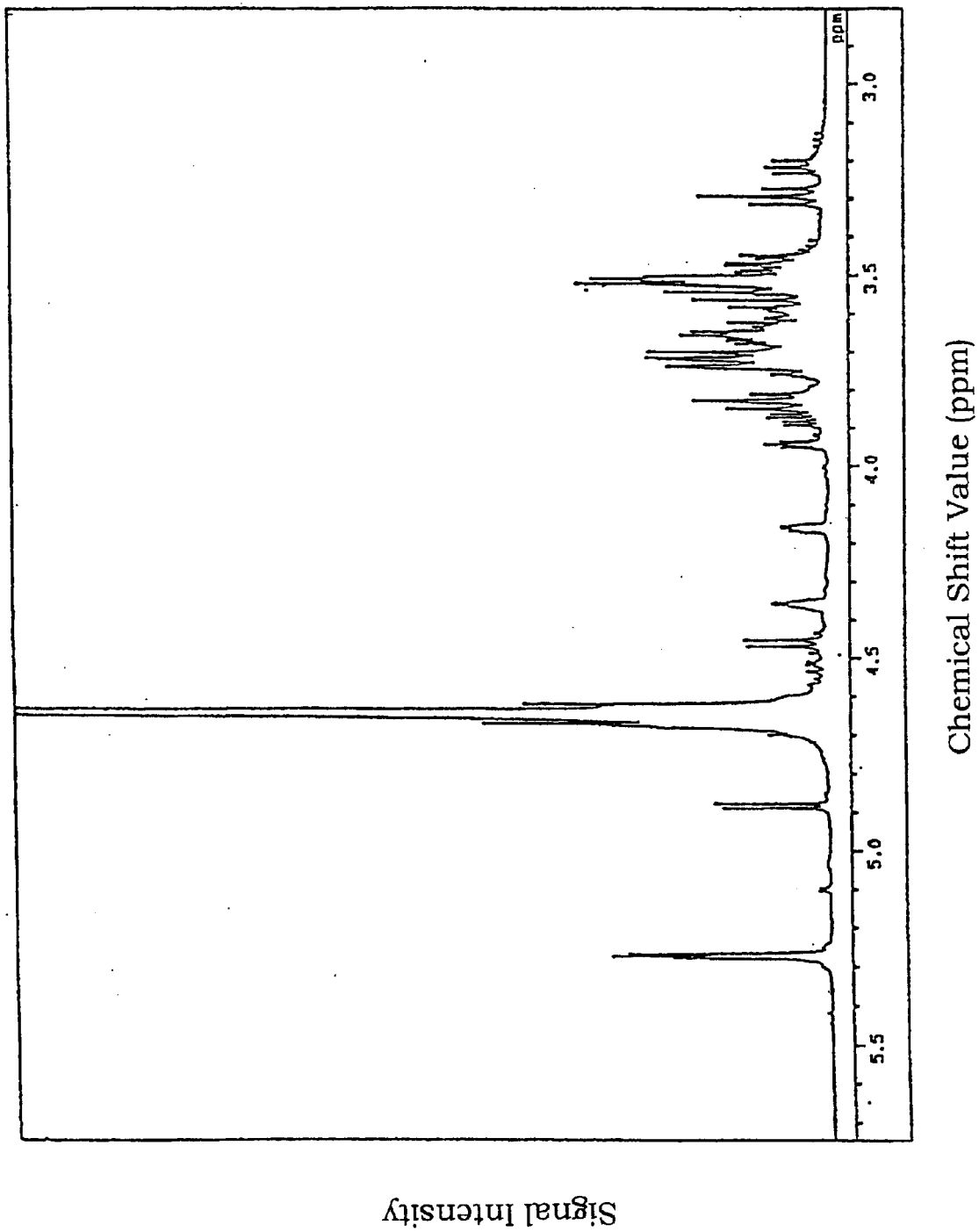
FIG. 7 illustrates the $^1$H-NMR spectrum of compound (14).

The sample was dissolved in heavy water. The results are expressed assuming the chemical shift value of HOD as 4.65 ppm. FIG. 7 illustrates the $^1$H-NMR spectrum of compound (14). In FIG. 7, the horizontal axis represents the chemical shift value (ppm) and the vertical axis represents the signal intensity.

The peak identification in $^1$H-NMR is as indicated in formula XI below.

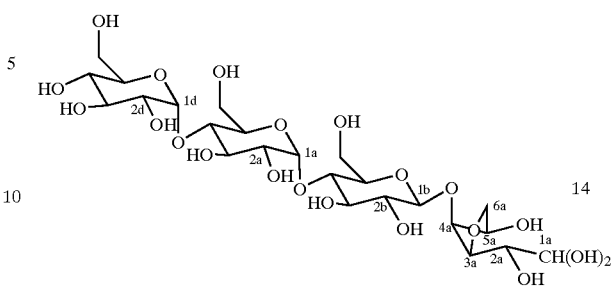

(XI)

FAB-MS m/z 649(M+H)$^+$ Glycerol was used for matrix.

(7) 4-O-benzyl-3,6-anhydro-D-galactose [compound (17)]

(i) 4-O-benzyl-1,2-O-isopropylidene-3,6-anhydro-D-galactose [compound (18)]

10 ml of dichloromethane was added to 200 mg (1 mmol) of the compound (3) under argon atmosphere. The mixture was cooled to −20° C. using ice/salt. 280 ml (1.5 mmol) of benzyl-2,2,2-trichloroacetoimidate (Tokyo Kasei; B1483) and 36 ml (0.2 mmol) $CF_3SO_3Si(CH_3)_3$/2 ml dichloromethane were slowly added thereto. The mixture was stirred at −20° C. for 1.5 hours. After saturated sodium hydrogencarbonate in water and ethyl acetate were added to the reaction mixture, organic layer was recovered. When this organic layer was subjected to thin-layer chromatography using hexane:ethyl acetate=6:1 as a developing solvent, a product of interest was detected at Rf value of about 0.2. The organic layer was dried over magnesium sulfate anhydrous, concentrated under reduced pressure and subjected to silica gel chromatography using hexane:ethyl acetate=6:1 as a developing solvent to obtain 87 mg of compound (18). The compound (18) was subjected to structural analysis by nuclear magnetic resonance (NMR) spectrometry.

$^1$H-NMR

δ 1.34(3H, s, Me), 1.52(3H, s, Me), 4.1(2H, m, H-6), 4.33(1H, dd, J=3, 4.5 Hz, H-2), 4.35(1H, d, J=3 Hz, H-4), 4.38(1H, m, H-5), 4.54(1H, d, J=4.5 Hz, H-3), 4.57(1H, d, J=12 Hz, —CH$_2$—), 4.65(1H, d, J=12 Hz, —CH$_2$—), 5.43 (1H, d, J=3 Hz, , H-1), 7.32(5H, m, Ph)

The sample was dissolved in heavy chloroform. The results are expressed assuming the chemical shift value of proton of chloroform as 7.24 ppm.

Figure 8:
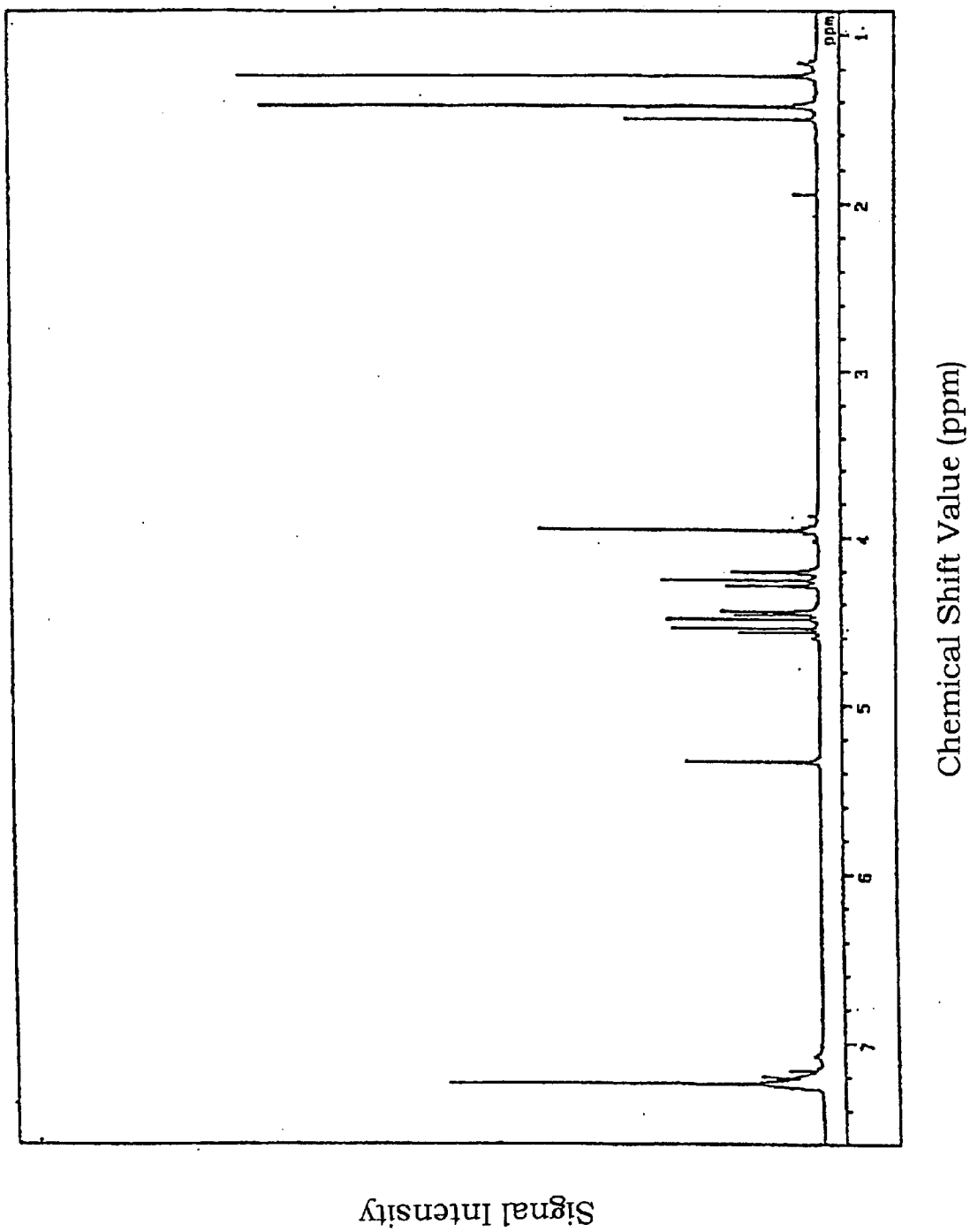
FIG. 8 illustrates the $^1$H-NMR spectrum of compound (18).

FIG. 8 illustrates the $^1$H-NMR spectrum of compound (18). In FIG. 8, the horizontal axis represents the chemical shift value (ppm) and the vertical axis represents the signal intensity.

(ii) Compound (17)

80 mg of the compound (18) was dissolved in 30 ml of dichloromethane. Trifluoroacetic acid/water (3.8 ml/0.2 ml) was added thereto. The mixture was stirred at room temperature for 3 hours. The reaction mixture was diluted with 300 ml of ethyl acetate and washed with sodium hydrogencarbonate in water. The organic layer was concentrated under reduced pressure and subjected to silica gel chromatography using chloroform:methanol=25:1 as a developing solvent to obtain 52 mg of compound (17) of formula XII below. The compound (17) was subjected to structural analysis by nuclear magnetic resonance (NMR) spectrometry (JNM-A500 (Nippon Denshi)) and mass spectrometry (MS) (DX302 mass spectrometer (Nippon Denshi)).

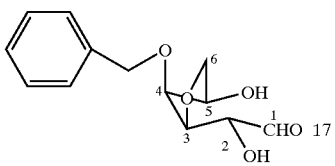

(XII)

¹H-NMR

Figure 9:
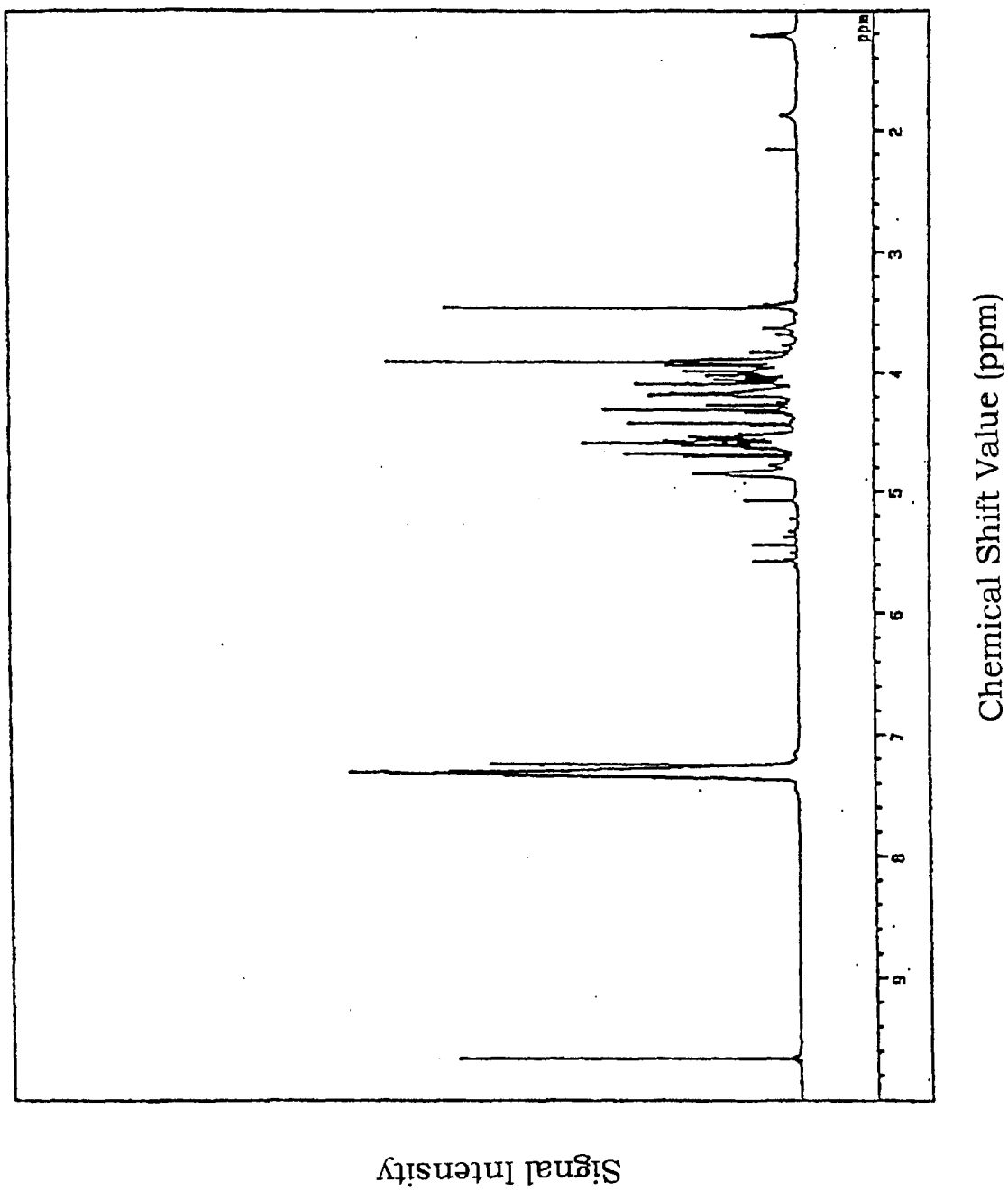
FIG. 9 illustrates the $^1$H-NMR spectrum of compound (17).

The compound (17) was dissolved in heavy chloroform. Structural analysis by nuclear magnetic resonance was carried out. FIG. 9 illustrates the ¹H-NMR spectrum of compound (17). In FIG. 9, the horizontal axis represents the chemical shift value (ppm) and the vertical axis represents the signal intensity.

Since the aldehyde at 1-position of 3,6-anhydro-D-galactose of this substance was in an equilibrium state with hemiacetal bond (α,β) in heavy chloroform, it was impossible to identify the signals. Disappearance of signals from 1,2-O-isopropylidene of the compound (18) (signals at δ 1.34 ppm and 1.52 ppm in FIG. 8) and generation of a signal from aldehyde (signal at δ 9.65 ppm in FIG. 9) were confirmed.

FAB-MS m/z 253(M+H)$^+$ Glycerol was used for matrix.

(8) 4-O-acetyl-3,6-anhydro-D-galactose [compound (19)]

(i) 4-O-acetyl-1,2-O-isopylidene-3,6-anhydro-D-galactose [compound (20)]

200 mg (1 mmol) of the compound (3), 113 ml (1.2 mmol) of acetic anhydride (Nacalai Tesque; Code. 042-24) and 24 mg (0.2 mmol) of 4-dimethylaminopyridine (Nacalai Tesque; Code. 129-22) were dissolved in 10 ml of dichloromethane. After cooling on ice, 166 ml (1.2 mmol) of triethylamine (Nacalai Tesque; Code. 348-05) was added thereto. The mixture was stirred at room temperature for 1 hour.

The reaction mixture was concentrated and subjected to silica gel chromatography using hexane:ethyl acetate=2:1 as a developing solvent to obtain 210 mg of compound (20). Structural analysis of the compound (20) was carried out by nuclear magnetic resonance (NMR) spectrometry (JNM-A500 (Nippon Denshi)).

¹H-NMR d1.30(3H, s, Me), 1.54(3H, s, Me), 2.02(3H, s, Ac), 3.93(1H, dd, J=3.5, 10 Hz, H-6), 4.05(1H, d, J=10 Hz, H-6), 4.24(1H, dd, J=3, 5 Hz, H-2), 4.37(1H, m, H-5), 4.48(1H, d, J=5 Hz, H-3), 5.38(1H, d, J=3 Hz, H-1), 5.40(1H, d, J=1.5 Hz, H-4)

The sample was dissolved in heavy chloroform. The results are expressed assuming the chemical shift value of proton of residual chloroform as 7.24 ppm.

Figure 10:
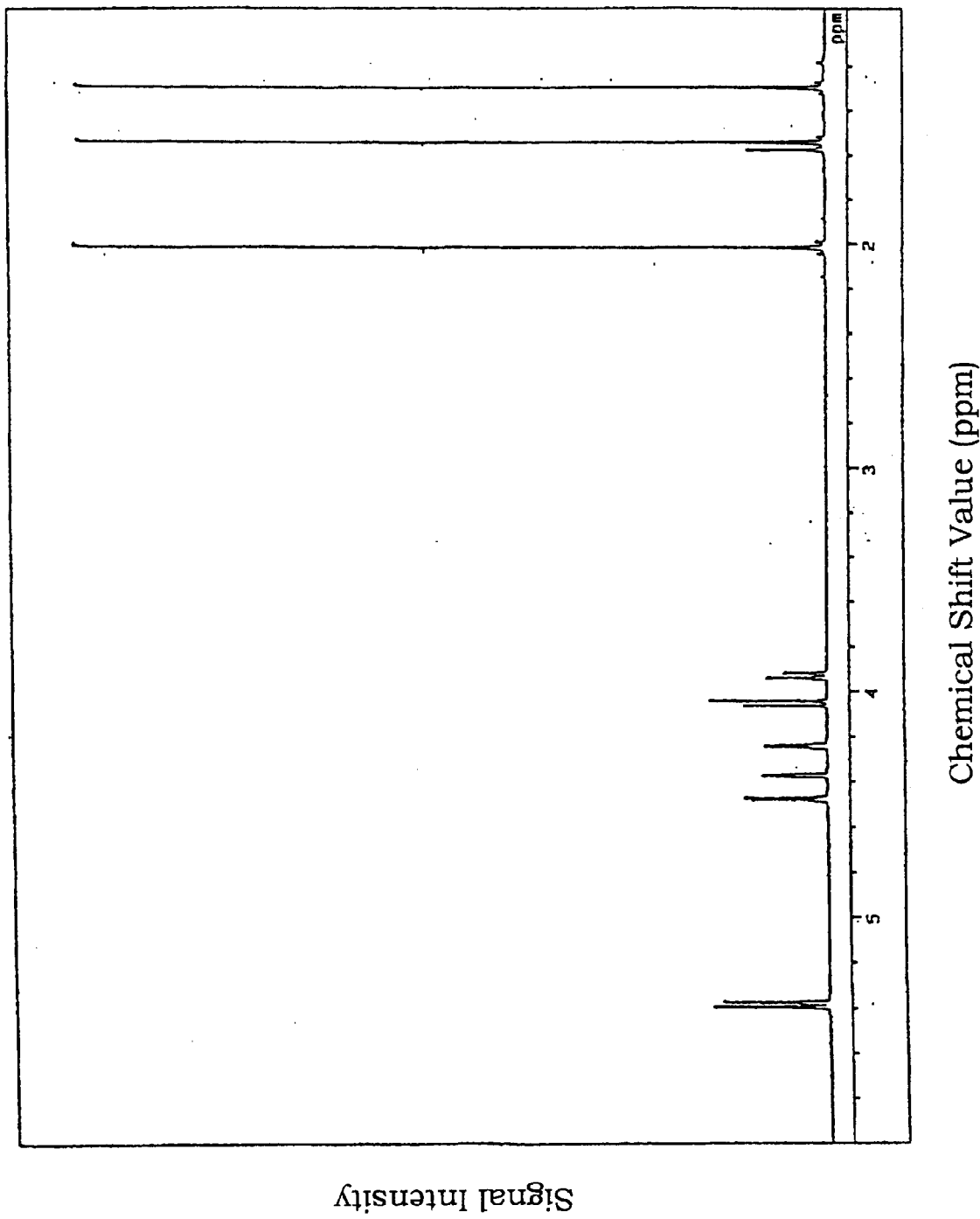
FIG. 10 illustrates the $^1$H-NMR spectrum of compound (20).

FIG. 10 illustrates the ¹H-NMR spectrum of compound (20). In FIG. 10, the horizontal axis represents the chemical shift value (ppm) and the vertical axis represents the signal intensity.

(ii) Compound (19)

200 mg of the compound (8) was dissolved in 15 ml of 70% acetic acid aqueous solution. The mixture was stirred at 95° C. for 2 hours. The reaction mixture was concentrated under reduced pressure and subjected to silica gel chromatography using chloroform:methanol=17:1 as a developing solvent to obtain 100 mg of compound (7). The compound (20) was subjected to structural analysis by nuclear magnetic resonance (NMR) spectrometry (JNM-A500 (Nippon Denshi)) and mass spectrometry (MS) (DX302 mass spectrometer (Nippon Denshi)). 1H-NMR d2.03(3H, s, Ac), 3.59(1H, dd, J=4, 6.5 Hz, H-2), 3.82 (1H, dd, J=1.5, 10 Hz, H-6), 3.87(1H, dd, J=4, 10 Hz), 3.99(1H, dt, J=4 Hz, H-3), 4.27(1H, ddt, J=1.5, 4 Hz), 4.89(1H, d, J=6.5 Hz, H-1), 5.01(1H, d, J=4 Hz, H-4) J=3, 10 Hz, H-3b), 5.35(1H, d, J=3.0 Hz, H-4b)

The sample was dissolved in heavy water. The results are expressed assuming the chemical shift value of HOD as 4.65 ppm.

Figure 11:
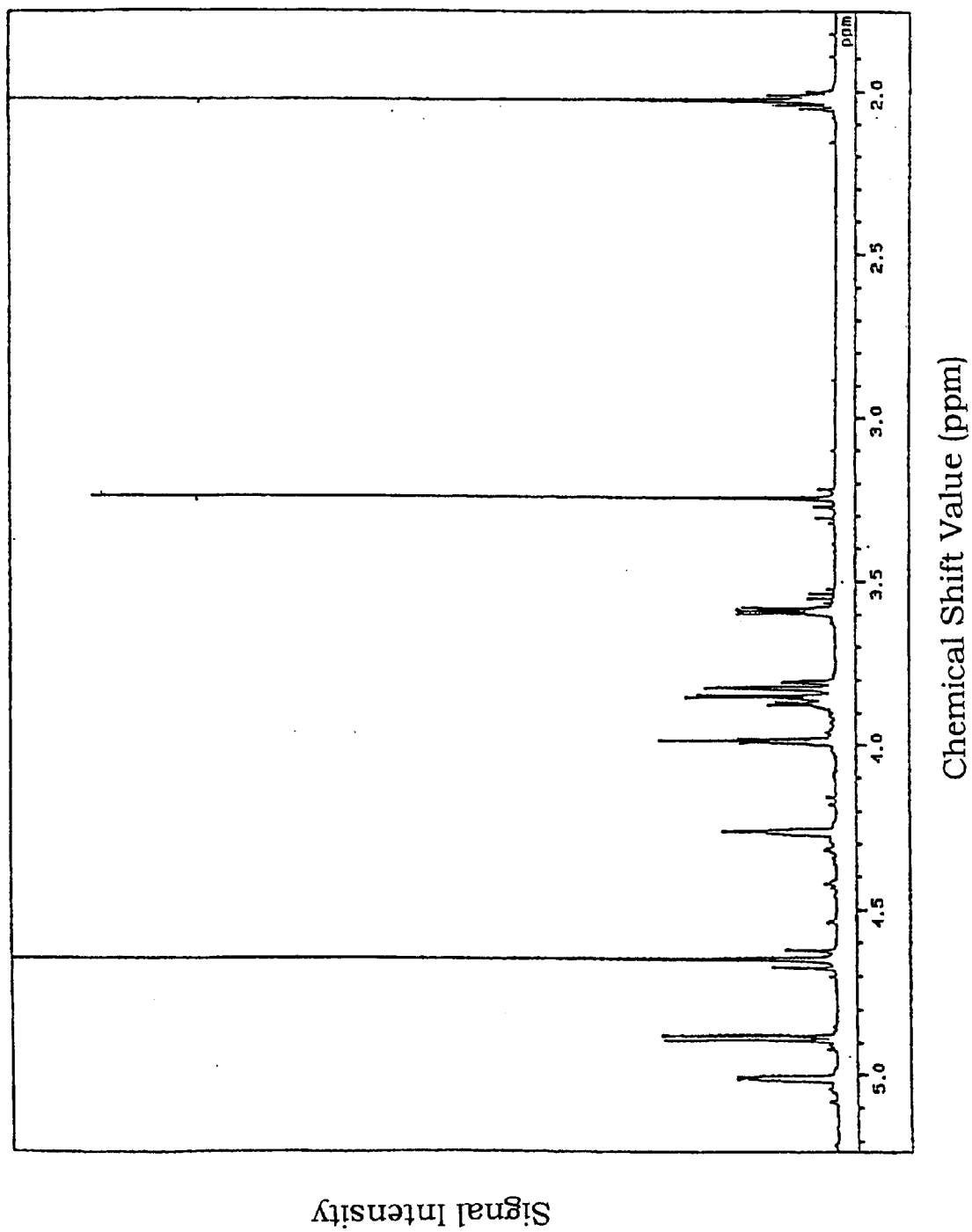
FIG. 11 illustrates the $^1$H-NMR spectrum of compound (19).

FIG. 11 illustrates the ¹H-NMR spectrum of compound (19). In FIG. 11, the horizontal axis represents the chemical shift value (ppm) and the vertical axis represents the signal intensity.

The peak identification in 1H-NMR is as indicated in formula XIII below.

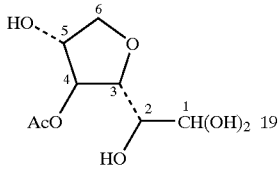

(XIII)

FAB-MS m/z 205(M+H)$^+$ Glycerol was used for matrix.

(9) 4-O-pentyl-3,6-anhydro-D-galactose [compound (21)]

(i) 4-O-pentyl-1,2-O-isopylidene-3,6-anhydro-D-galactose [Compound (22)]

200 mg (1 mmol) of the compound (3) was dissolved in 4 ml of dimethylformamide. 30 mg (1.2 mmol) of sodium hydride (Nacalai Tesque; Code. 042-24) was added thereto while cooling on ice. The mixture was stirred at room temperature for 30 minutes. 260 ml (2 mmol) of pentane iodide (Tokyo Kasei; I0066) was added thereto while cooling on ice. The mixture was stirred for 1 hour.

The reaction mixture was washed and concentrated and then subjected to silica gel chromatography using hexane-:ethyl acetate=8:1 as a developing solvent to obtain 270 mg of compound (22). Structural analysis of the compound (22) was carried out by nuclear magnetic resonance (NMR) spectrometry (JNM-A500 (Nippon Denshi)).

¹H-NMR d0.87(3H, m, H-11), 1.29(4H, m, H-9, 10), 1.33(3H, s, Me), 1.56(2H, m, H-8), 1.56(3H, s, Me), 3.50(2H, m, H-7), 3.98(1H, dd, J=3, 10 Hz, H-6), 4.02(1H, d, J=10 Hz, H-6), 4.28(1H, dd, J=3, 5 Hz, H-2), 4.36(1H, m, H-5), 4.46(1H, d, J=5 Hz, H-3), 5.41(1H, d, J=3 Hz, H-1)

The sample was dissolved in heavy chloroform. The results are expressed assuming the chemical shift value of proton of residual chloroform as 7.24 ppm.

Figure 12:
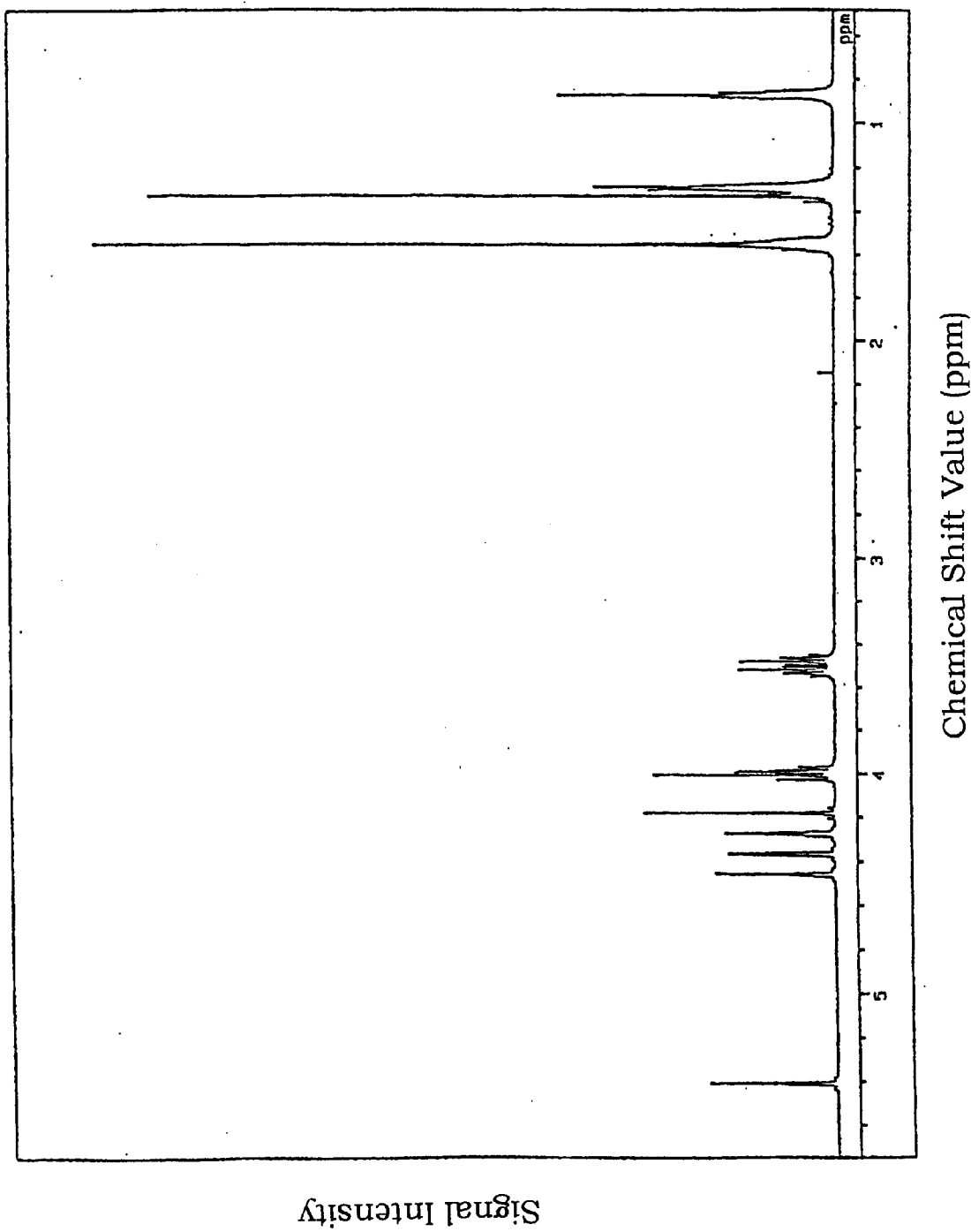
FIG. 12 illustrates the $^1$H-NMR spectrum of compound (22).
Figure 13:
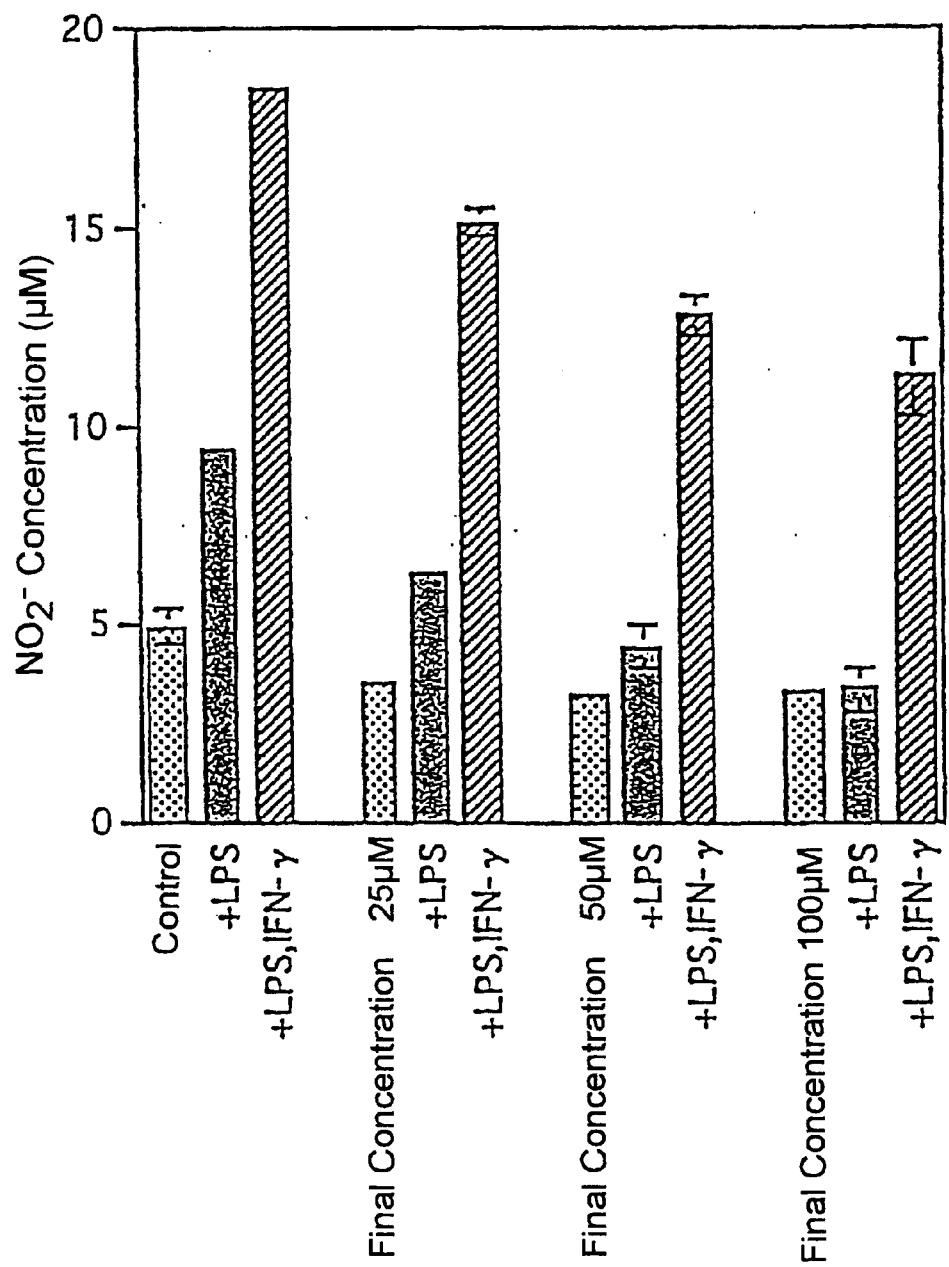
FIG. 13 illustrates the $NO_2^-$ concentration in a culture medium obtained by culturing with the addition of compound (2).
Figure 14:
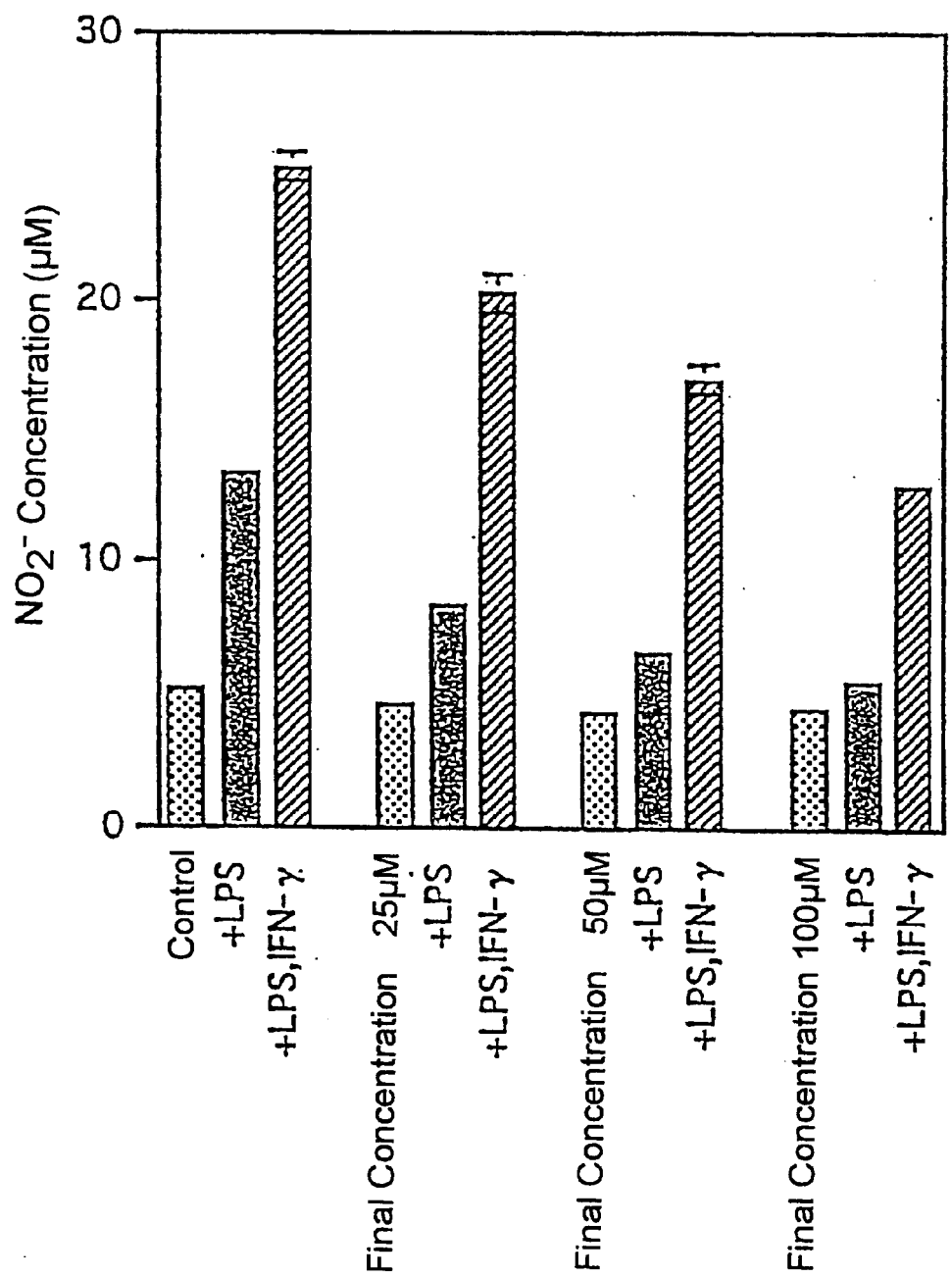
FIG. 14 illustrates the $NO_2^-$ concentration in a culture medium obtained by culturing with the addition of compound (7).
Figure 1:
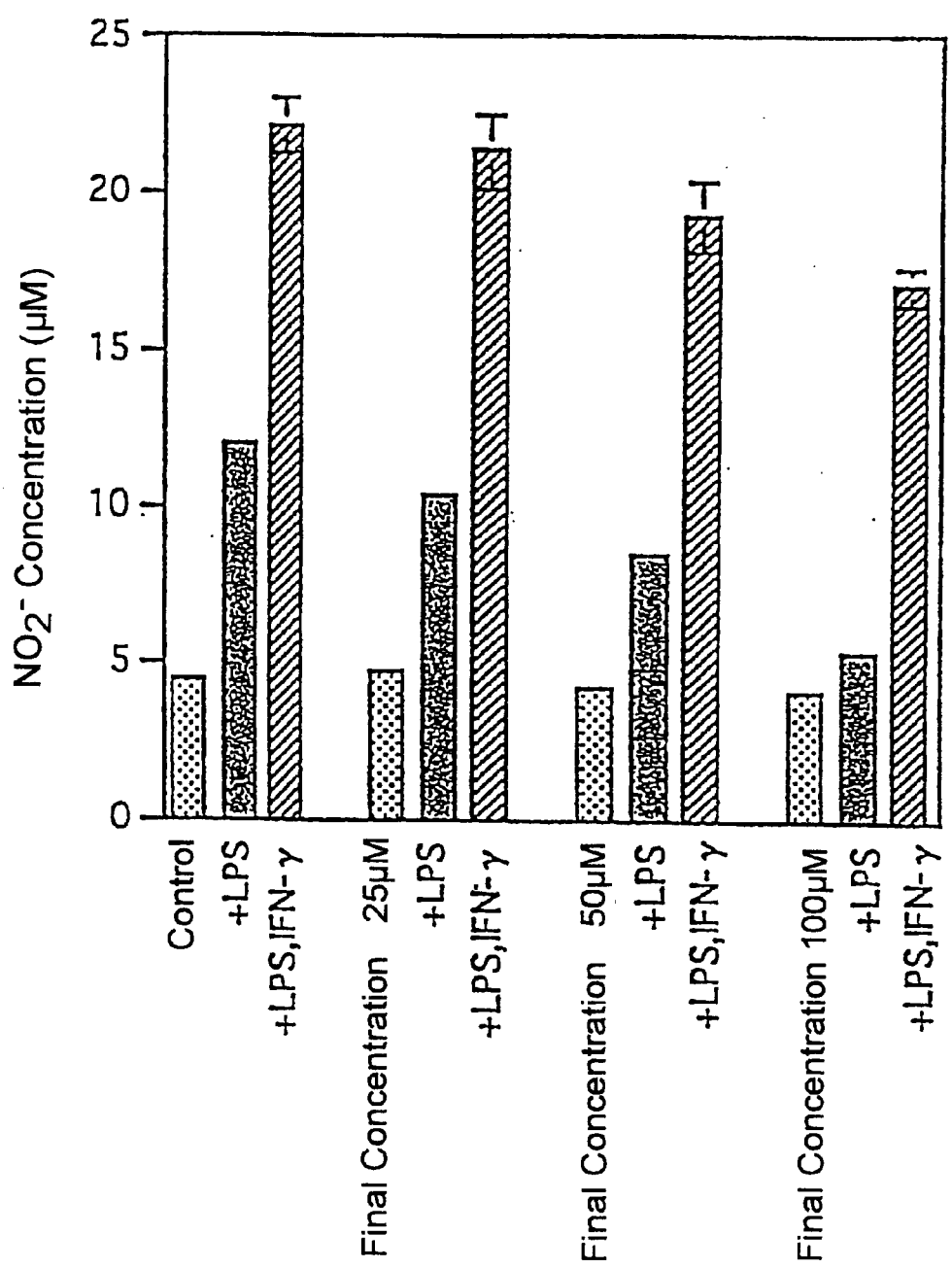
Figure 16:
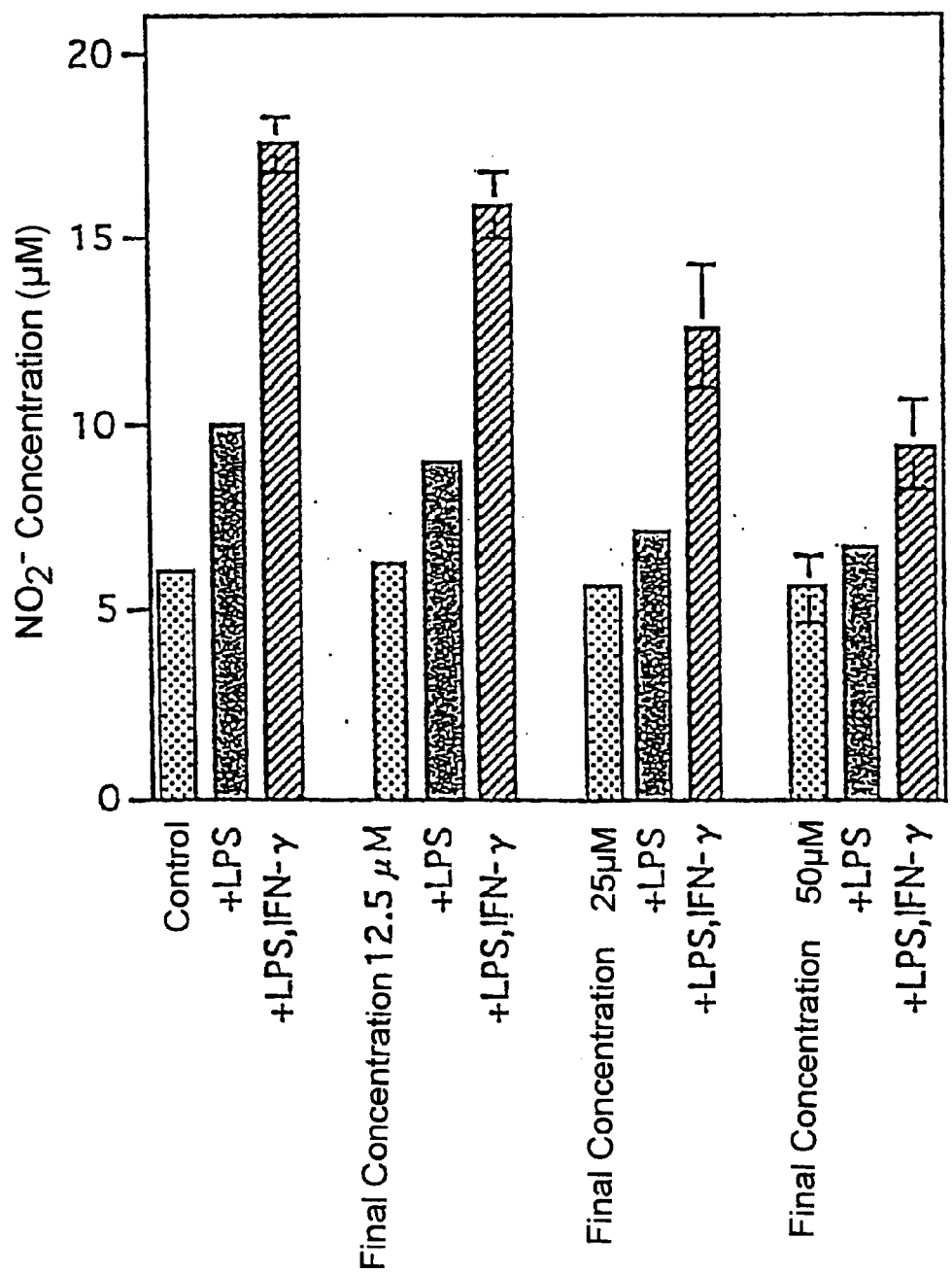
FIG. 16 illustrates the $NO_2^-$ concentration in a culture medium obtained by culturing with the addition of compound (11).
Figure 17:
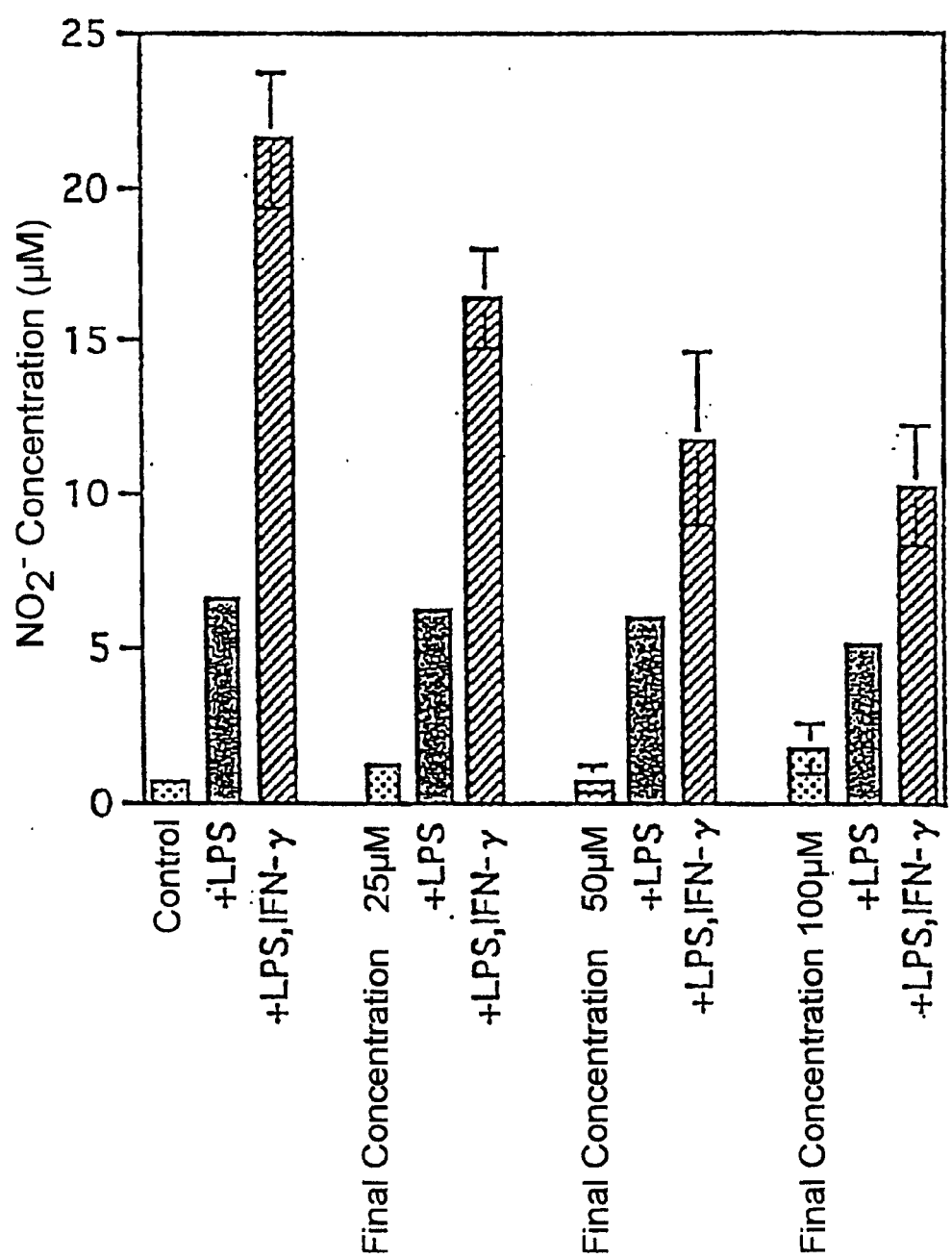
FIG. 17 illustrates the $NO_2^-$ concentration in a culture medium obtained by culturing with the addition of compound (14).
Figure 18:
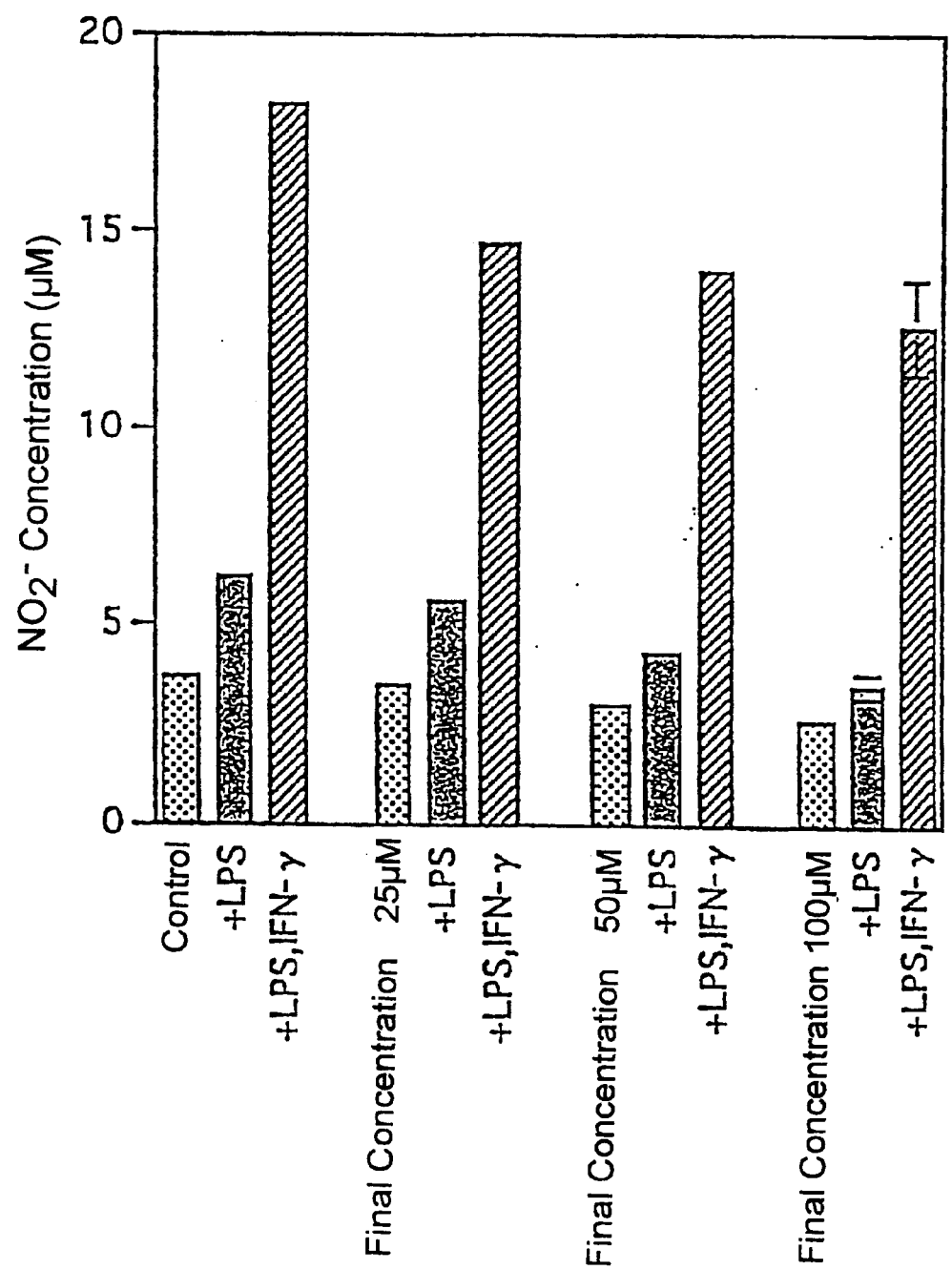
FIG. 18 illustrates the $NO_2^-$ concentration in a culture medium obtained by culturing with the addition of compound (17).
Figure 19:
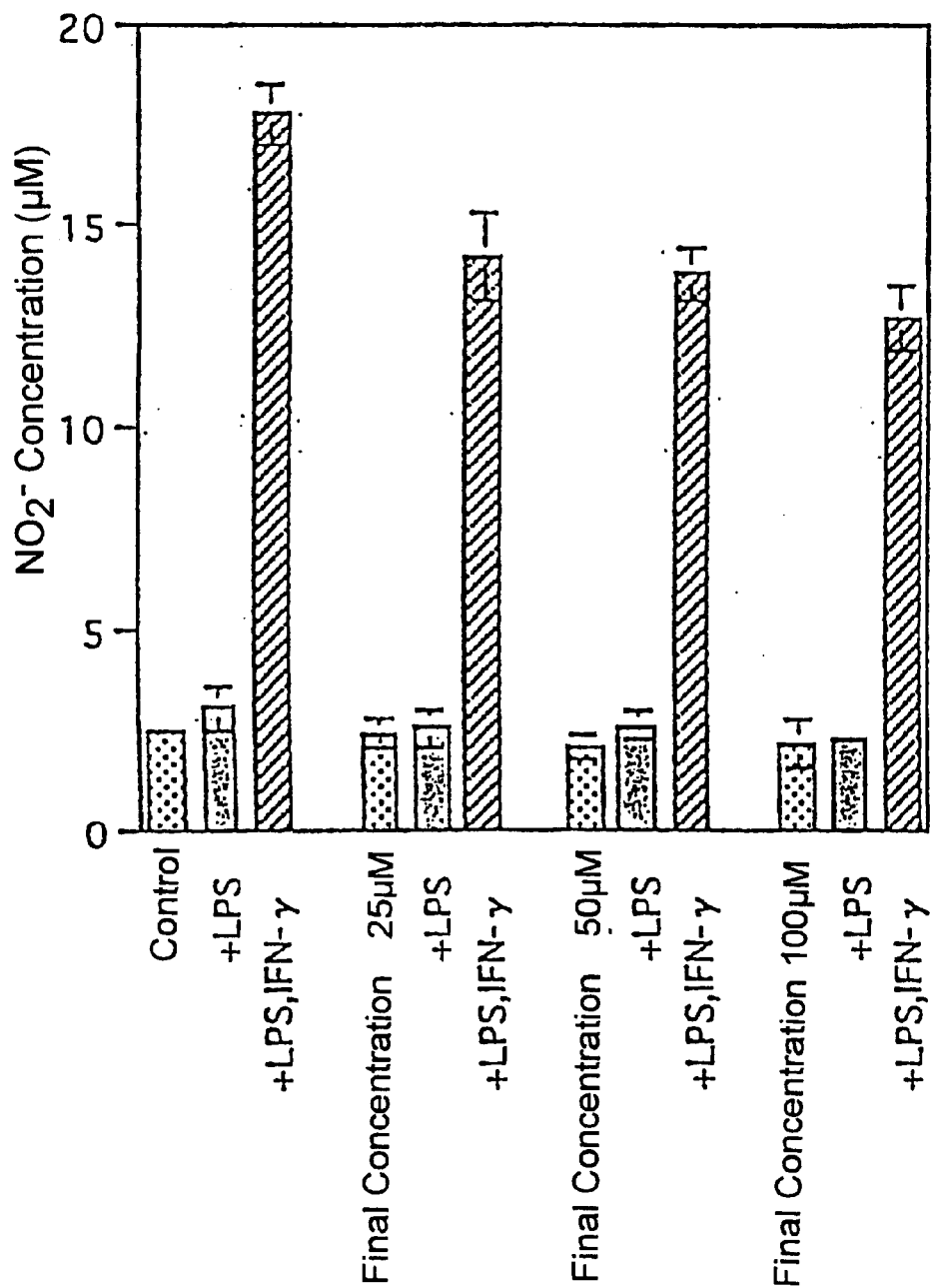
FIG. 19 illustrates the $NO_2^-$ concentration in a culture medium obtained by culturing with the addition of compound (19).
Figure 20:
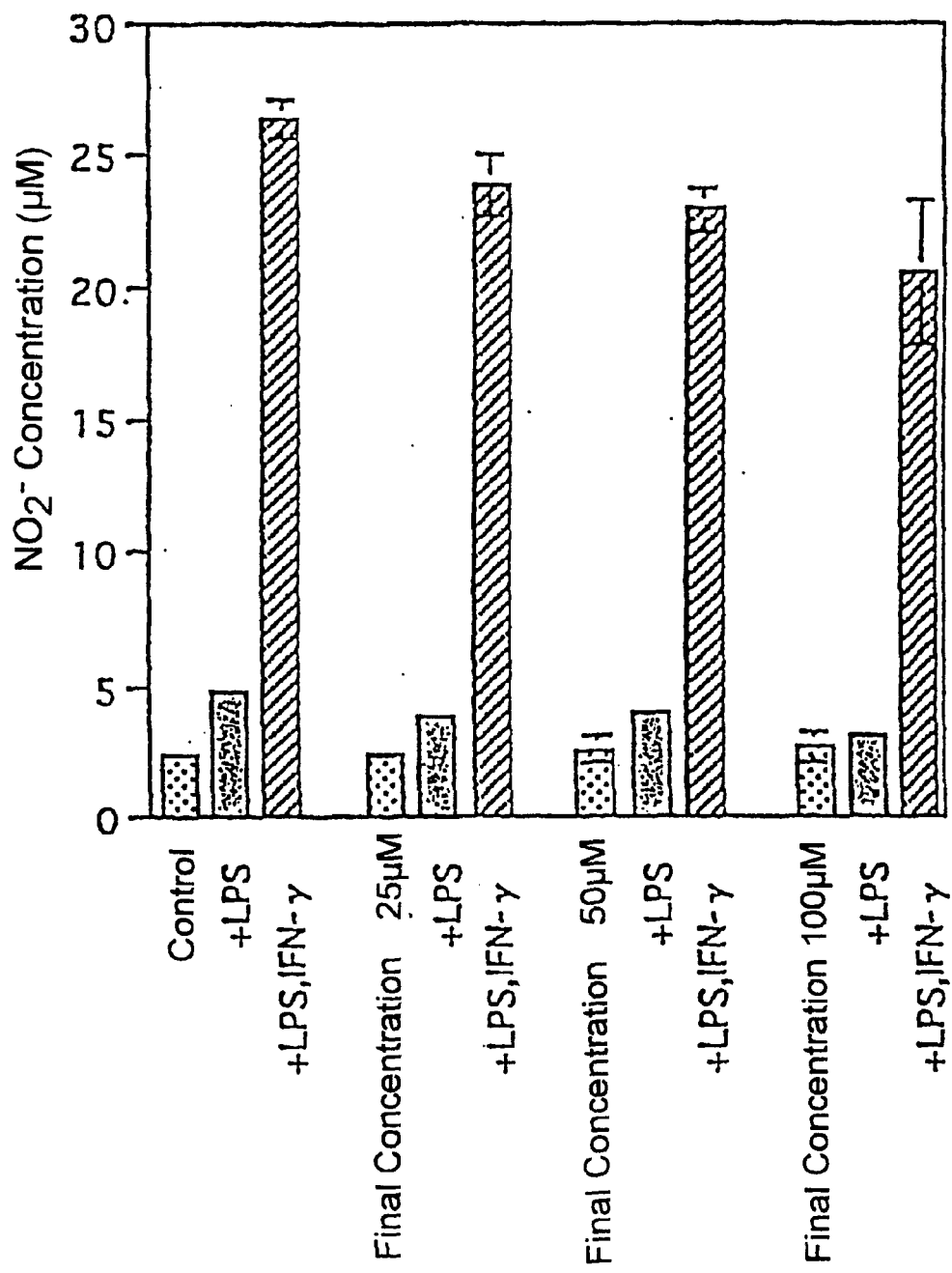
FIG. 20 illustrates the $NO_2^-$ concentration in a culture medium obtained by culturing with the addition of compound (21).

FIG. 12 illustrates the ¹H-NMR spectrum of compound (22). In FIG. 12, the horizontal axis represents the chemical shift value (ppm) and the vertical axis represents the signal intensity.

(ii) Compound (21)

270 mg of the compound (22) was dissolved in 30 ml of dichloromethane. Trifluoroacetic acid/water (2.85 ml/0.15 ml) was added thereto. The mixture was stirred at room temperature for 3 hours. The reaction mixture was diluted with 300 ml of ethyl acetate and washed with sodium hydrogencarbonate in water. The organic layer was concentrated under reduced pressure and subjected to silica gel chromatography using chloroform:methanol=25:1 as a developing solvent to obtain 100 mg of compound (21). The compound (21) was subjected to structural analysis by mass spectrometry (MS) (DX302 mass spectrometer (Nippon Denshi)). The chemical formula of the compound (21) is shown in formula XIV below.

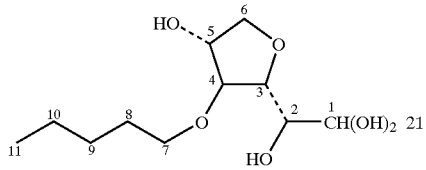

(XIV)

FAB-MS
m/z 233 (M+H)$^+$ Glycerol was used for matrix.

Example 2

The compound (7) or the compound (9) synthesized in Example 1 was dissolved at a final concentration of 10 mM in RPMI 1640 medium supplemented with 10% calf serum. These samples were allowed to stand at 37° C. for 4 hours. 1 ml each of the samples was then subjected to thin-layer chromatography using chloroform:methanol=5:1 as a developing solvent. Detection was carried out using orcinol-sulfuric acid.

For each sample, a spot with Rf value of 0.5, the same value as that for the compound of general formula IV in which Z is CH$_2$OH and Y is H (L-glycero-1,5-epoxy-1α,β,6-dihydroxy-cis-hex-3-en-2-one, hereinafter referred to as DGE), was detected.

Furthermore, conversion into DGE was also observed for the compound (2), the compound (11), the compound (14) and the compound (17) synthesized in Example 1.

Example 3

Human promyelocytic leukemia HL-60 cells (ATCC CCL-240) were cultured at 37° C. in RPMI 1640 medium (Gibco) containing 10% of fetal calf serum (JRH Bioscience) which had been treated at 56° C. for 30 minutes, and suspended in the same medium at a concentration of 5000 cells/90 μl. Each 90 μl portion of the suspension was distributed into each well of a 96-well plate (Falcon). To the suspension in each well was added 10 μl of one the following samples, and incubated at 37° C. in the presence of 5% CO$_2$. The samples were 2-, 4-, 8-, 16-, 32-, 64- or 128-dilutions of filter-sterilized 200 mM aqueous solution of the compound (2) obtained in Example 1, 50 mM aqueous solution of the compound (7), 50 mM aqueous solution of the compound (9), 100 mM aqueous solution of the compound (11), 100 mM aqueous solution of the compound (14), 20 mM aqueous solution of the compound (17), 12.5 mM aqueous solution of the compound (19) or 12.5 mM aqueous solution of the compound (21) with sterile water, as well as water. After 48 hour from the initiation of the incubation, the numbers of viable cells calculated based on the absorbance measured according to the MTT method as described in "Apoptosis Jikken Protocol" (Syuzyun-sha, Seiichi Tanuma, ed., pp. 156 (1994)) were compared each other.

As a result, the compounds (2), (7), (9), (11), (14), (17), (19) and (21) exhibited antiproliferation activities against the human promyelocytic leukemia HL-60 cells. The concentration at which 50% of the proliferation is inhibited (IC$_{50}$) was calculated based on these results, and is shown in Table 1.

TABLE 1

|  | IC$_{50}$ (μM) |
| --- | --- |
| Compound (2) | 860 |
| Compound (7) | 104.18 |
| Compound (9) | 112.72 |
| Compound (11) | 145.55 |
| Compound (14) | 113.32 |
| Compound (17) | 204.62 |
| Compound (19) | 320 |
| Compound (21) | 160 |

Example 4

HL-60 (ATCC CCL-240) cells were cultured at 37° C. in RPMI 1640 medium (Bio Whittaker) containing 10% fetal calf serum (JRH) which had been treated at 56° C. for 30 minutes and suspended in RPMI 1640 medium at a concentration of 2.5×10$^5$ cells/4.5 ml.

500 ml each of aqueous solutions of the compound (2) at a concentration of 10, 50 or 100 mM, the compound (7) at a concentration of 500, 1000 or 1500 μM, the compound (9) at a concentration of 750, 1500 or 3000 μM, the compound (11) at a concentration of 750, 1500 or 3000 μM, or the compound (14) at a concentration of 750, 1500 or 3000 μM was added to 4.5 ml of the suspension. The mixtures were incubated at 37° C. for 24 hours in the presence of 5% CO$_2$.

The cultured cells were examined under an optical microscope. Condensation of nuclei, shrinking of cells and formation of apoptotic bodies were observed for the cells cultured with the addition of the compound (2) at a final concentration of 5 mM or more, the compound (7) at a final concentration of 100 μM or more, the compound (9) at a final concentration of 150 μM or more, the compound (11) at a final concentration of 150 μM or more, or the compound (14) at a final concentration of 150 μM or more. No such phenomenon was observed for the control cells cultured with the addition of 500 ml of saline.

Measurement of apoptotic cells using FACScan as described in Saibo Kogaku, Bessatsu (Cell Technology, Suppl.) Jikken Protocol Series: Apoptosis Jikken Protocol (Experimental Protocol Series: Experimental Protocols for Apoptosis) (Shujun-sha) pp. 129–130 and analysis of DNA fragmentation as described in Bio Manual UP Series: Saishin Apoptosis Jikken-ho (Bio Manual UP Series: Current Experimental Methods for Apoptosis) (Yodo-sha) pp. 61–63 were carried out using cells cultured for 24 or 48 hours in the same manner as that described above. As a result, apoptotic cells were observed for cells cultured in the presence of the compound (2) at a final concentration of 5 mM or more for 24 hours, the compound (7) at a final concentration of 100 μM or more, the compound (9) at a final concentration of 150 μM or more, the compound (11) at a final concentration of 150 μM or more, or the compound (14) at a final concentration of 150 μM or more. DNA fragmentation was observed for cells cultured in the presence of the compound (2) at a final concentration of 5 mM or more for 24 hours or at a final concentration of 1 mM or more for 48 hours, the compound (7) at a final concentration of 100 μM or more, the compound (9) at a final concentration of 150 μM or more for 24 hours, the compound (11) at a final concentration of 150 μM or more, or the compound (14) at a final concentration of 75 μM or more. No such phenomenon was observed for the control cells cultured with the addition of 500 ml of saline.

Example 5

A portion of the cells cultured for 24 or 48 hours as described in Example 4 was stained with 0.4% Trypan Blue and examined under an optical microscope. The number of viable cells which were not stained and the number of dead cells which were stained blue were counted. The concentration of each of the compounds (2), (7), (9), (11) and (14) that results in a viability of 50% (Viability$_{50}$ mM) was determined. The results are shown in Table 2.

TABLE 2

|  | 24 hours | 48 hours |
| --- | --- | --- |
| Compound (2) | 18130 | 3400 |
| Compound (7) | 122.96 | 101.19 |
| Compound (9) | 17247.65 | 189.06 |
| Compound (11) | 1264.18 | 152.43 |
| Compound (14) | 550.85 | 150.47 |

As described above, a great difference between the Viability$_{50}$ at 24 hours and the Viability$_{50}$ at 48 hours was observed for some of the compounds, whereas no difference was observed for others. The differences reflect the rate of introducing unsaturated bonds at 3-position and 4-position of anhydrogalactose after elimination of the R group or the time required for exhibiting the activity (e.g., the absorption rate). As shown by the results, the timing of the exertion of the physiological activity can be controlled by changing R. It is considered that the Viability$_{50}$ at 48 hours represents the degree of the ultimate physiological activity. The degree of exertion of the physiological activity can be similarly controlled by changing R.

Example 6

RAW264.7 cells (ATCC TIB 71) were suspended in Dulbecco's modified Eagle's medium (Bio Whittaker, 12-917F) without Phenol Red containing 10% fetal calf serum (Gibco) and 2 mM L-glutamine (Life Technologies Oriental, Code. 25030-149) at a concentration of 3×10$^5$ cells/ml. 500 µl of the suspension was added to each well of a 48-well microtiter plate and the plate was incubated at 37° C. for 12 hours in the presence of 5% $CO_2$.

10 µl of 25 µg/ml lipopolysaccharide (LPS, Sigma, Code. L-2012), or 10 µl of 2.5 µg/ml LPS and 10 µl of 500 U/ml interferon-γ (IFN-γ, a product of Genzyme sold by Cosmobio, Code. MG-IFN), and 10 µl of one the aqueous solutions containing the compound (2) at a concentration of 1.25, 2.5 or 5.0 mM, the compound (7) at a concentration of 1.25, 2.5 or 5.0 mM, the compound (9) at a concentration of 1.25, 2.5 or 5.0 mM, the compound (11) at a concentration of 0.625, 1.25 or 2.5 mM, the compound (14) at a concentration of 1.25, 2.5 or 5.0 mM, the compound (17) at a concentration of 1.25, 2.5 or 5.0 mM, the compound (19) at a concentration of 1.25, 2.5 or 5.0 mM, or the compound (21) at a concentration of 1.25, 2.5 or 5.0 mM as a sample were added to the well. The plate was incubated for additional 12 hours. The concentration of $NO_2^-$ resulting from oxidation of NO in the medium was then measured. As control groups, a group to which LPS or IFN-γ was not added and a group to which no sample was added were provided.

After cultivation, 100 µl of 4% Griess' reagent (Sigma, Code. G4410) was added to 100 µl of the medium, and the mixture was allowed to stand for 15 minutes at room temperature. The absorbance at 490 nm was then measured.

$NO_2^-$ concentration in the medium was calculated with reference to a calibration curve prepared by using $NaNO_2$ dissolved in the same medium at a predetermined concentration. All of the measurements were carried out in triplicate.

As a result, the compound (2) at a final concentration of 25 µM or more, the compound (7) at a final concentration of 25 µM or more, the compound (9) at a final concentration of 50 µM or more, the compound (11) at a final concentration of 25 µM or more, the compound (14) at a final concentration of 25 µM or more, the compound (17) at a final concentration of 50 µM or more, the compound (19) at a final concentration of 25 µM or more, or the compound (21) at a final concentration of 25 µM or more inhibited NO production induction by LPS or LPS and IFN-γ.

The results are shown in FIGS. 13 to 20. FIGS. 13, 14, 15, 16, 17, 18, 19 and 20 illustrate the $NO_2^-$ concentrations in the culture medium obtained by culturing with the addition of the compound (2), the compound (7), the compound (9), the compound (11), the compound (14), the compound (17), the compound (19) and the compound (21), respectively. In FIGS. 13 to 20, the horizontal axes represent the culture conditions and the vertical axes represent the $NO_2^-$ concentrations (µM).

Example 7

RAW264.7 cells were suspended in Dulbecco's modified Eagle's medium (Bio Whittaker, Code. 12-604F) containing 10% fetal calf serum at a concentration of 3×10$^5$ cells/ml. 500 µl of the suspension was added to each well of a 48-well microtiter plate and the plate was incubated at 37° C. for 6 hours in the presence of 5% $CO_2$. The compound (7), (14) or (17) prepared in Example 1 was added to the well at a final concentration of 50, 100 or 100 µM, respectively. The plate was incubated for additional 5 hours. 10 µl of 50 µg/ml lipopolysaccharide (LPS, Sigma, Code. L-2012) aqueous solution was then added to the well. After the plate was incubated for additional 12 hours, the amount of prostaglandin $E_2$ was measured. As control groups, a group to which LPS was not added and a group to which the compound (7), (14) or (17) was not added were provided.

After cultivation, the amount of prostaglandin $E_2$ in the culture supernatant was measured using Prostaglandin $E_2$ ELISA Kit (Neogen, Code. 404110). All of the measurements were carried out in triplicate.

Figure 21:
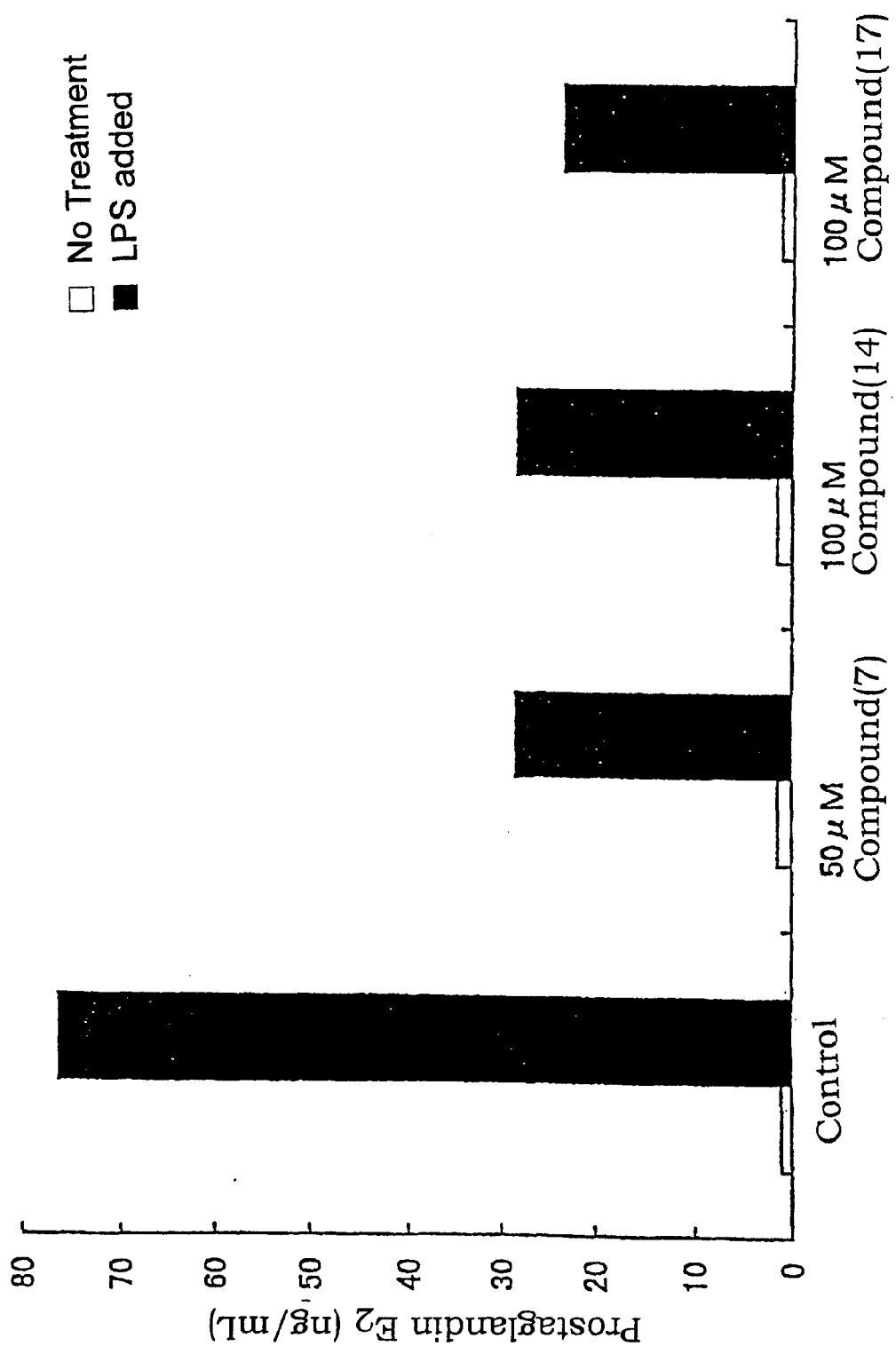
FIG. 21 illustrates the $PGE_2$ concentration in a culture medium obtained by culturing under various culture conditions.

As a result, each of the compounds (7), (14) and (17) inhibited the prostaglandin $E_2$ production induction by LPS. The results are shown in FIG. 21. FIG. 21 illustrates the prostaglandin $E_2$ concentration in the medium obtained by incubating under various culture conditions. In FIG. 21, the horizontal axis represents the culture conditions and the vertical axis represents the prostaglandin $E_2$ concentration (ng/ml).

Example 8

The compound (7) in Example 1 was suspended in olive oil (Nacalai Tesque) at a concentration of 1% to prepare a 1% suspension of the compound (7).

The 1% suspension of the compound (7) prepared as described above was administered to ddY mice (Japan SLC, female, 7 weeks old) by forced oral administration once a day, 12 times in 15 days, at a dosage of 10 or 30 ml/kg. Tap water was similarly administered by forced oral administration as a control. Each group consisted of 3 mice. Thereafter, 4 ml of RPMI 1640 medium (Bio Whittaker, Code. 12-702F) containing 10% fetal calf serum was intraperitoneally injected. Media removed from 3 mice after extensive massage were combined to obtain celiac cells. The celiac cells were suspended in RPMI 1640 medium containing 10% fetal calf serum at a concentration of 10$^6$ cells/ml. 500 µl of the suspension was added to each well of a 48-well microtiter plate and the plate was incubated at 37° C. for 2 hours in the presence of 5% $CO_2$. Adhesive cells obtained by removing the culture supernatant were used as celiac macrophages. 500 µl of fresh Dulbecco's modified Eagle's medium (Bio Whittaker, Code. 12-917F) without Phenol Red containing 10% fetal calf serum and 2 mM L-glutamine was added to each well. 10 µl of an aqueous solution containing lipopolysaccharide (LPS, Sigma, Code. L-2012) at a concentration of 5 µg/ml and interferon-γ (IFN-γ, sold by Cosmobio, Code. GZM-MG-IFN) at a concentration of 2000 U/ml was added to the well. The plate was incubated for additional 12 hours. The concentration of $NO_2^-$ resulting from oxidation of NO in the medium was then measured as described in Example 6. As a control group, a group to which the aqueous solution of LPS and IFN-γ was not added was provided. All of the measurements were carried out in triplicate.

As a result, a remarkable activity of inhibiting NO production was observed for the celiac macrophages prepared from mice to which the compound (7) was orally administered at 10 or 30 ml/kg. The agar oligosaccharide exhibited a strong activity of inhibiting NO production when freely given as drinking water.

Figure 22:
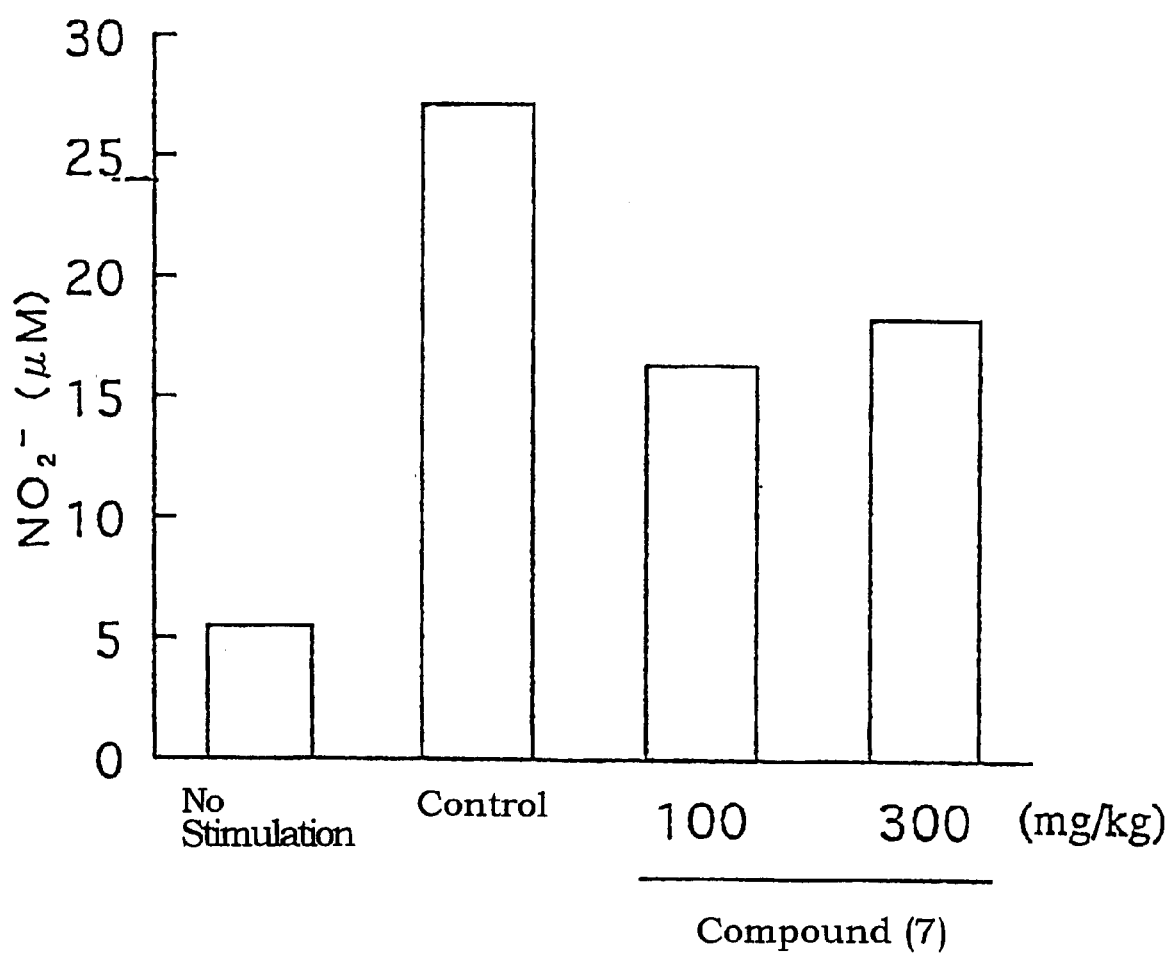
FIG. 22 illustrates the $NO_2^-$ concentration in a culture medium obtained by culturing under various culture conditions.

The results are shown in FIG. 22. FIG. 22 illustrates the $NO_2^-$ concentrations in the medium incubated under various culture conditions. The horizontal axis the represents the culture conditions and the vertical axis represents the $NO_2^-$ concentration (µM).

Example 9

The compound (7) in Example 1 was suspended in olive oil (Nacalai Tesque) at a concentration of 1% to prepare a 1% suspension of the compound (7).

The 1% suspension of the compound (7) prepared as described above was administered to ddY mice (Japan SLC, female, 7 weeks old) by forced oral administration once a day, 12 times in 15 days, at a dosage of 10 or 30 ml/kg. Tap water was similarly administered by forced oral administration as a control. Each group consisted of 3 mice. Thereafter, 4 ml of RPMI 1640 medium (Bio Whittaker, Code. 12-702F) containing 10% fetal calf serum was intraperitoneally injected. Media removed from 3 mice after extensive massage were combined to obtain celiac cells. The celiac cells were suspended in RPMI 1640 medium containing 10% fetal calf serum at a concentration of $10^6$ cells/ml. 500 µl of the suspension was added to each well of a 48-well microtiter plate and the plate was incubated at 37° C. for 2 hours in the presence of 5% $CO_2$. Adhesive cells obtained by removing the culture supernatant were used as celiac macrophages. 500 µl of fresh Dulbecco's modified Eagle's medium (Bio Whittaker, Code. 12-604F) containing 10% fetal calf serum was added to each well. 10 µl of 50 µg/ml lipopolysaccharide (LPS, Sigma, Code. L-2012) aqueous solution was added to the well. After the plate was incubated for additional 12 hours, the amount of prostaglandin $E_2$ ($PGE_2$) was measured. As a control group, a group to which LPS was not added was provided.

After cultivation, the amount of prostaglandin $E_2$ in the culture supernatant was measured using Prostaglandin $E_2$ ELISA Kit (Neogen, Code. 404110). All of the measurements were carried out in triplicate.

As a result, a remarkable activity of inhibiting $PGE_2$ production was observed for the celiac macrophages prepared from mice to which the compound (7) was orally administered at 10 or 30 ml/kg. The agar oligosaccharide exhibited a strong activity of inhibiting $PGE_2$ production when freely given as drinking water.

Figure 23:
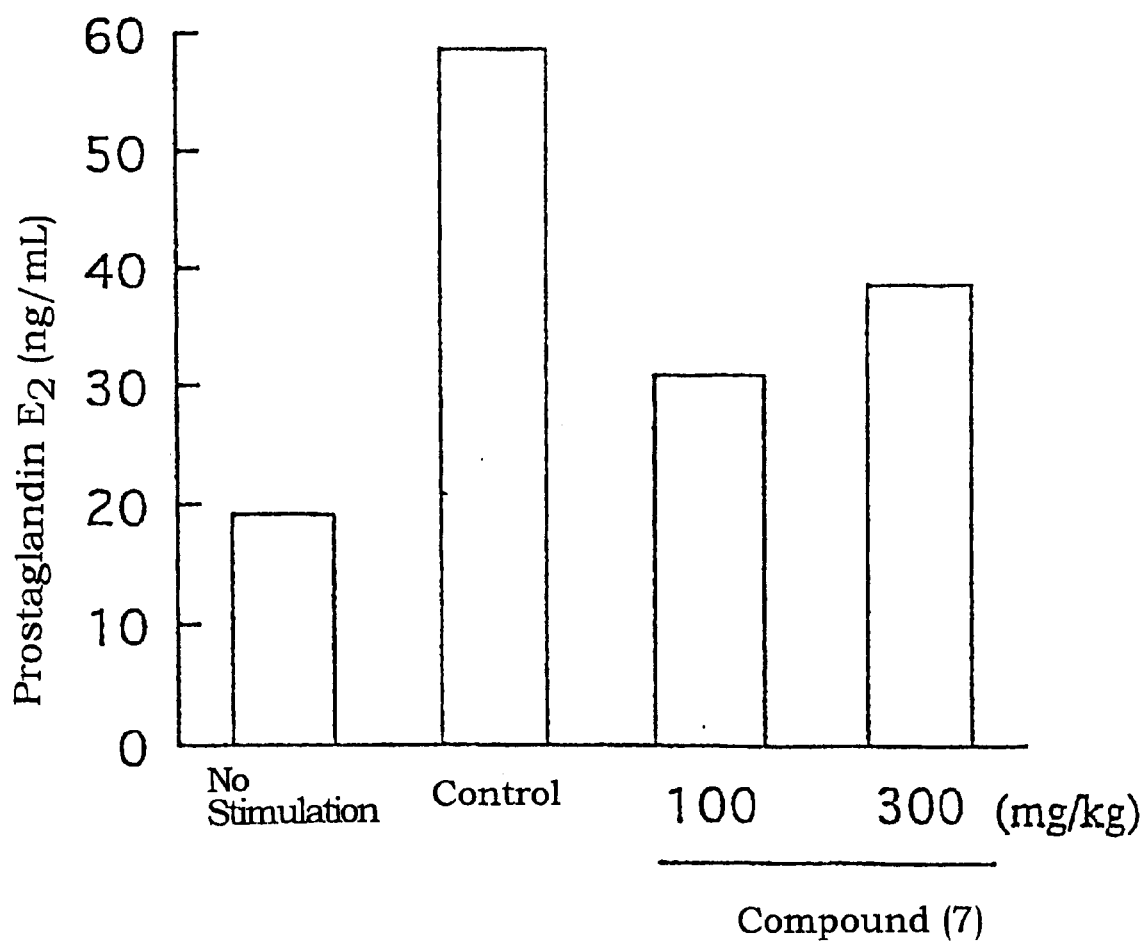
FIG. 23 illustrates the $PGE_2$ concentration in a culture medium obtained by culturing under various culture conditions.

The results are shown in FIG. 23. FIG. 23 illustrates the $PGE_2$ concentrations in the medium incubated under various culture conditions. The horizontal axis the represents the culture conditions and the vertical axis represents the $PGE_2$ concentration (ng/ml)

Example 10

HL-60 cells (ATCC CCL-240) were suspended in RPMI 1640 medium (Bio Whittaker, 12-702F) containing 10% fetal calf serum (Gibco) and 100 µM hydroxyurea at a concentration of $5\times10^5$ cells/ml. 20 ml of the suspension was added to a 10-cm Petri dish. The dish was incubated at 37° C. overnight in the presence of 5% $CO_2$ to make the cells arrest at G1 phase. The cells were collected by centrifugation and resuspended in RPMI 1640 medium containing 10% fetal calf serum (Gibco) and 100 µM hydroxyurea at a concentration of $5\times10^5$ cells/ml. 5 ml of the suspension was added to each well of a 6-well microtiter plate. On the other hand, as cells without the treatment with hydroxyurea, HL-60 cells were suspended in RPMI 1640 medium containing 10% fetal calf serum (Gibco) at a concentration of $1\times10^5$ cells/ml. 5 ml of the suspension was added to each well of a 6-well microtiter plate. 50 µl of a solution containing DGE at a concentration of 30, 22.5, 15 or 7.5 mM in water, 25 µl of a solution containing the compound (7) at a concentration of 60, 45, 30 or 15 mM in dimethyl sulfoxide, or 25 µl of a solution containing the compound (17) at a concentration of 100, 75, 50 or 25 mM in dimethyl sulfoxide was added to the well containing the cells treated with hydroxyurea. 50 µl of a solution containing DGE at a concentration of 8, 6, 4 or 2 mM in water, 25 µl of a solution containing the compound (7) at a concentration of 30, 22.5, 15 or 7.5 mM in dimethyl sulfoxide, or 25 µl of a solution containing the compound (17) at a concentration of 80, 60, 40 or 20 mM in dimethyl sulfoxide was added to the well containing the cells without the treatment with hydroxyurea. The plate was incubated for additional 48 hours. Cells collected by centrifuging the culture were suspended in 5 ml of fresh RPMI 1640 medium containing 10% fetal calf serum (Gibco). 100 µl of the suspension was used for measuring viable cell number using Premix WST-1 Cell Proliferation Assay System (Takara Shuzo, MK400).

For each of the samples, the concentration at which 50% of the proliferation is inhibited ($IC_{50}$) for the cells treated with hydroxyurea was higher than that for the cells without the treatment with hydroxyurea. The results are shown in Table 3. Table 3 summarizes $IC_{50}$ (µM) for each of the samples. These results demonstrate that DGE and precursor compounds of DGE such as the compound (7) and the compound (17) (referred to as R-AhGal compounds) are less toxic to cells arrested at G1 phase. Since most of cells in a living body are arrested at G1 phase, it is considered that DGE and R-AhGal compounds (precursors of DGE) are agents less toxic to a living body.

TABLE 3

| | Cells treated with hydroxyurea (µm) | Cells without treatment with hydroxyurea (µm) |
|---|---|---|
| DGE | 101.2 | 49.5 |
| Compound (7) | 150.6 | 79.1 |
| Compound (17) | 264.5 | 189.8 |

Example 11

(1) Establishment of conditions for detecting DGE by gas chromatography 2 mg of DGE and 2 mg of 2-deoxy-glucose (Nacalai Tesque, Code. 107-22) as an internal standard were dissolved in 200 µl of water. 3 equivalents of NaBH$_4$ were added thereto for reduction at room temperature for 4 hours. The reaction mixture was neutralized using acetic anhydride and concentrated to dryness. 1 ml of pyridine, 1 ml of acetic anhydride and 4-dimethylaminopyridine were added thereto for acetylation reaction for 1 hour while sonicating. The reaction mixture was diluted with 2 ml of chloroform. Saturated sodium hydrogencarbonate solution was added thereto while cooling on ice to stop the reaction. The organic layer was washed several times with cold water, dried over magnesium sulfate anhydrous and concentrated to dryness. The resulting reaction product (alditol acetate derivative) was dissolved in acetone and analyzed by gas chromatography under the following conditions.

Instrument: shimadzu-17A (Shimadzu);

Column: Ultra 2 Capillary Column (0.32 mm×25 m) (Hewlett-Packard);

Temperature: 160→220° C., 3° C./minute;

Detection: FID.

Figure 24:
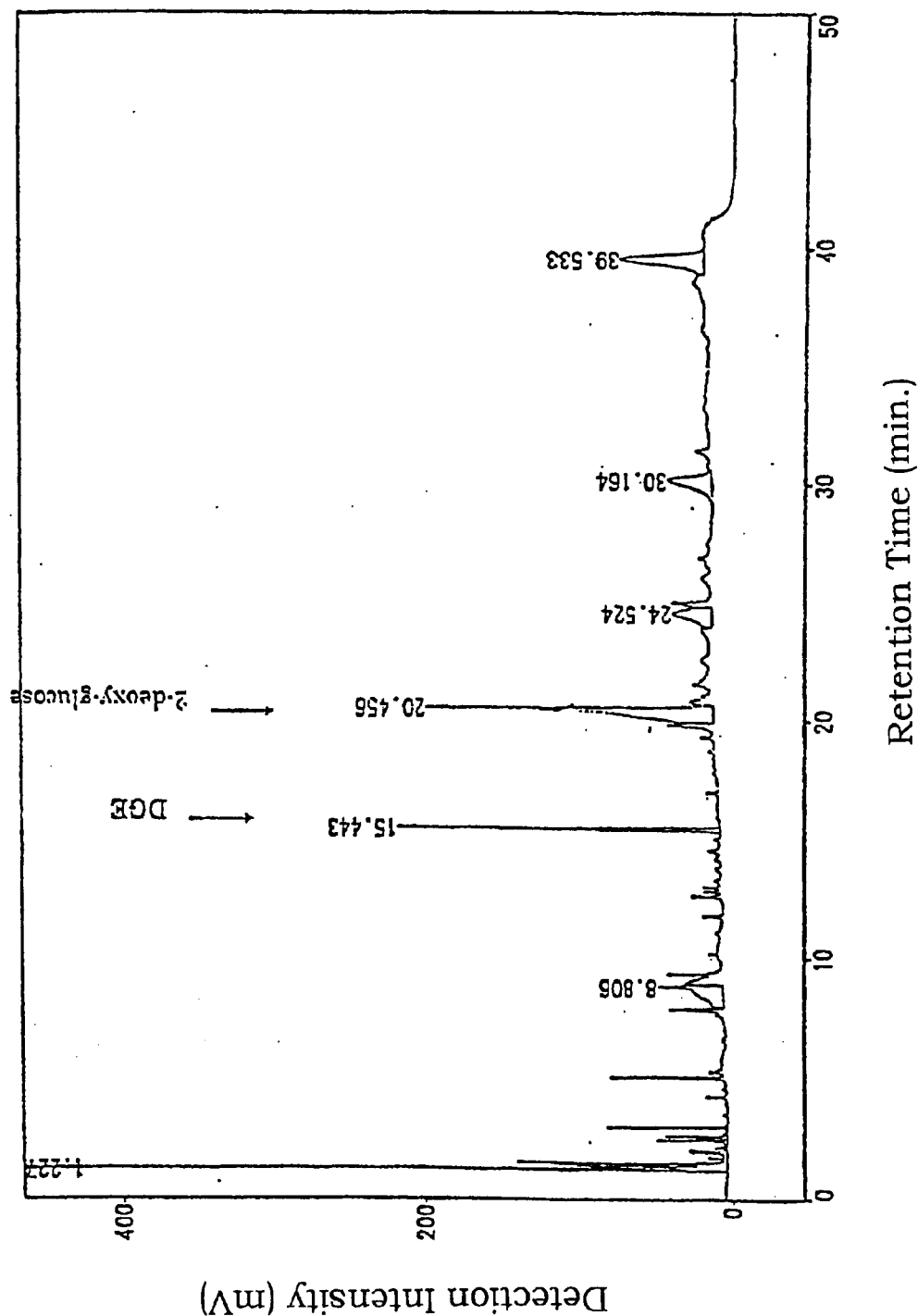
FIG. 24 illustrates the results of gas chromatography.

As a result, DGE and 2-deoxy-glucose were detected at 15.443 minutes and 20.456 minutes, respectively. The results are shown in FIG. 24. FIG. 24 illustrates the results of gas chromatography. The vertical axis represents the detection intensity (mV) and the horizontal axis represents the retention time (minutes).

Figure 25:
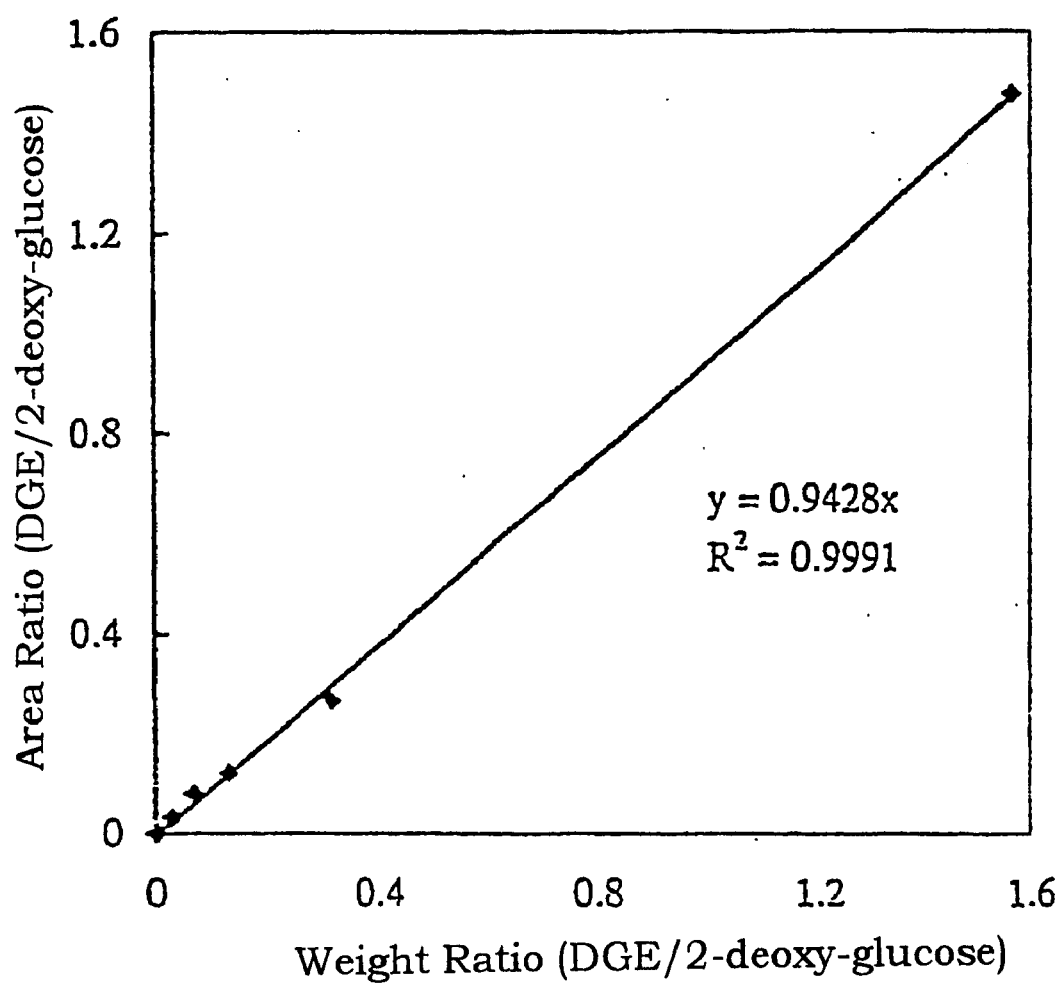
FIG. 25 illustrates a calibration curve of area ratio of DGE to an internal standard versus corresponding weight ratio of DGE to the internal standard.

(2) Preparation of calibration curve 0.5, 2.5, 12.5, 62.5 or 312.5 µg of a highly purified product of DGE and 20, 20, 200, 200 or 200 µg of 2-deoxyglucose as an internal standard were mixed together and dissolved in 100 µl of culture medium. 4.0 equivalents of NaBH$_4$ was added thereto for reduction at room temperature for 4 hours. Preliminary experiments had confirmed that no difference is observed for 3.0 to 10 equivalents. The respective samples were subjected to similar procedures for conversion into alditol acetate derivatives and analyzed by gas chromatography under conditions as described above. Based on the results of gas chromatography, a calibration curve was prepared for the area ratio of DGE to the internal standard versus corresponding weight ratio of DGE to the internal standard. The results are shown in FIG. 25. FIG. 25 illustrates a calibration curve of area ratio of DGE to the internal standard versus corresponding weight ratio of DGE to the internal standard. The vertical axis represents the area ratio of DGE to the internal standard and the horizontal axis represents the weight ratio of DGE to the internal standard.

(3) Quantification of DGE generated from respective compounds in culture medium 1 to 3 mg of the compound (2) (◊), (7) (×) (11) (▲), (14) (■), (17) (●), (19) (*) or (21) (|), or agarobiose (♦) was dissolved in 1 ml of culture medium. The solutions were incubated at 37° C. 200 µl of the medium was collected over time (4, 8, 12, 24 or 48 hours). The procedures as described above were carried out immediately after the collection. The resulting alditol acetate derivatives were analyzed by gas chromatography under conditions as described above. The amount of DGE was calculated using the calibration curve based on the area ratio of DGE to the internal standard determined from the results.

Figure 26:
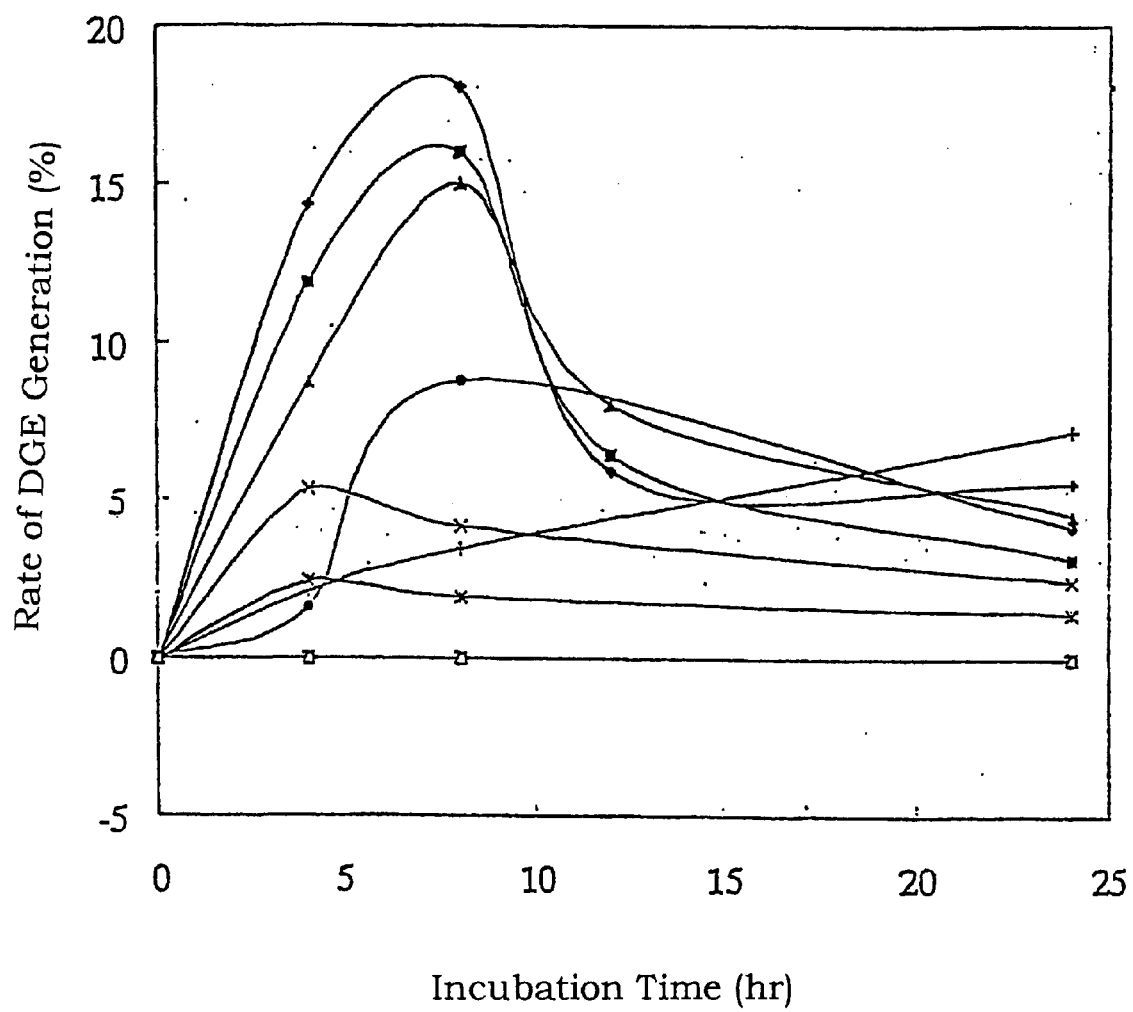
FIG. 26 illustrates the time course of conversion rate from each of the compounds into DGE.

Time course of conversion rate of each of the compounds into DGE as determined based on these results is shown in FIG. 26. FIG. 26 illustrates the time course of conversion rate from each of the compounds into DGE. The vertical axis represents the generation rate (%) and the horizontal axis represents the incubation time (hour).

Example 12

RAW264.7 cells (ATCC TIB 71) were suspended in Dulbecco's modified Eagle's medium (Bio Whittaker, 12-604F) containing 10% fetal calf serum (Gibco) at a concentration of 3×10$^5$ cells/ml. 0.5 ml of the suspension was added to each well of a 48-well microtiter plate and the plate was incubated at 37° C. overnight in the presence of 5% CO$_2$. 5 µl of a solution containing the compound (14) at a concentration of 10 mM in water, 1 µl of a solution of the compound (7) at a concentration of 25 mM in dimethyl sulfoxide, or 1 µl of a solution of the compound (17) at a concentration of 50 mM in dimethyl sulfoxide was added to the well. After incubation for additional 5 hours, 5 µl of a solution of lipopolysaccharide (LPS, Sigma, L-2012) at a concentration of 100 µg/ml in water was added thereto. After incubation for 18 hours, a culture supernatant was collected. The content of interleukin 10 (IL-10) in the culture supernatant was measured using enzyme immuno sandwich assay (ELISA; Mouse IL-10 ELISA Kit, Endogen). As a control, a group to which the sample or the LPS aqueous solution was not added was provided. All of the measurements were carried out in duplicate.

Figure 27:
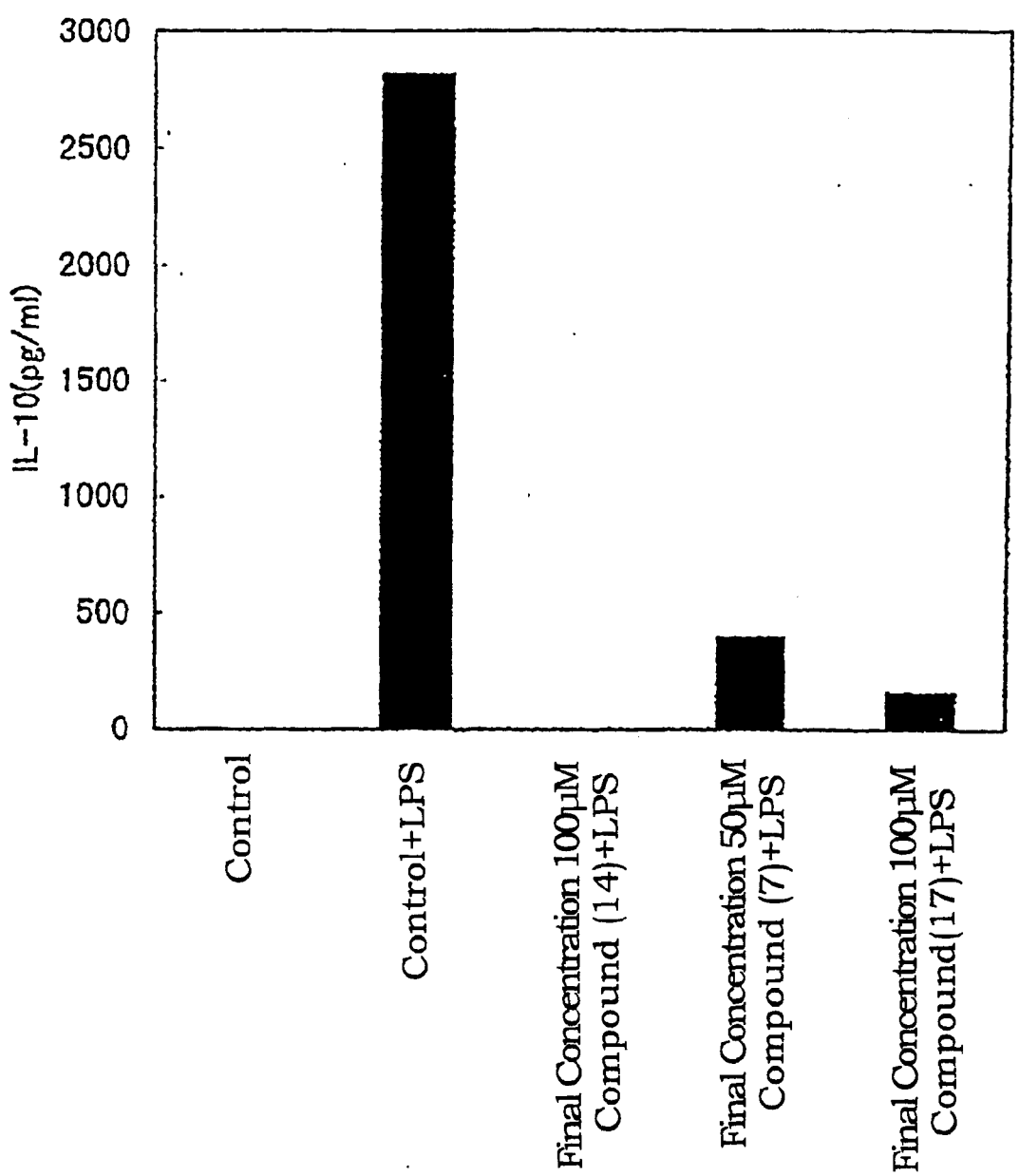
FIG. 27 illustrates the IL-10 concentrations in culture supernatants obtained by culturing under various culture conditions.

As a result, inhibition of LPS-induced IL-10 production was observed for cells to which the compound (14), the compound (7) or the compound (17) was added. The results are shown in FIG. 27. FIG. 27 illustrates the IL-10 concentrations in culture supernatants obtained by culturing under various culture conditions. The horizontal axis represents the culture conditions and the vertical axis represents the IL-10 concentration (pg/ml).

When experiments were carried out to determined the effects of these compounds on 12-O-tetradecanoylphorbol 13-acetate (TPA)-induced interleukin 6, inhibition of TPA-induced IL-6 production was observed.

Example 13

RAW264.7 cells (ATCC TIB 71) were suspended in Dulbecco's modified Eagle's medium (Bio Whittaker, 12-604F) containing 10% fetal calf serum (Gibco) at a concentration of 3×10$^5$ cells/ml. 5 ml of the suspension was added to each well of a 6-well microtiter plate and the plate was incubated at 37° C. overnight in the presence of 5% CO$_2$. 50 µl of a solution containing the compound (11) or the compound (14) at a concentration of 10 mM or 5 mM in water, 5 µl of a solution containing the compound (7) at a concentration of 50 mM or 25 mM in dimethyl sulfoxide, or 5 µl of a solution containing the compound (17) at a concentration of 100 mM or 50 mM in dimethyl sulfoxide was added to the well. The plate was incubated for 12 hours. A positive control for heme oxygenase 1 induction in which 5 µl of 3 mM solution of 15-deoxy-Δ12,14 prostaglandin J$_2$ (Cayman Chemical, 18570) in dimethyl sulfoxide was added, and a negative control in which water was added were provided. The cells were recovered by detaching the cells from the plate using a scraper and suspended in 0.1 M tris-HCl buffer (pH 7.5) containing 0.05 mM pepstatin A (Sigma, P5318), 0.2 mM leupeptin (Sigma, L2884), 1 mM phenylmethylsulfonyl fluoride (Nacalai Tesque, 273-27), 10 mM ethylenediaminetetraacetic acid disodium salt and 0.1% Triton X-100. A supernatant obtained by centrifuging the suspension after freezing and thawing was used as a protein fraction. The content of protein in the protein fraction was determined using Micro BCA Protein Assay Reagent (a product of Pierce sold by Takara Shuzo, P7411). A sample from the protein fraction prepared as described above was mixed with an equal volume of 0.125 M tris-hydrochloride buffer (pH 6.8) containing 4% sodium lauryl sulfate (SDS), 2% 2-mercaptoethanol, 0.001% Bromophenol Blue and 20% glycerol. After treatment at 100° C. for 5 minutes, a portion corresponding to 10 μg of protein was loaded on 12.5% SDS-polyacrylamide gel and electrophoresed at a constant current of 20 mA. After electrophoresis, the gel was transferred to a PVDF membrane (Millipore, IPVH000 10) at a constant voltage of 15 V for 25 minutes using a blotting buffer (containing 48 mM tris, 39 mM glycine, 20% methanol and 0.0375% SDS) and Trans-Blot SD Cell Semi-Dry blotting apparatus (Bio-Rad) according to the attached protocol. After transferring, the PVDF membrane was blocked in a solution of Block Ace (Dainippon Pharmaceutical, UK-B25) at 4 C overnight. After blocking, the membrane washed three times in phosphate buffered saline containing 0.1% Tween 20 for 15 minutes with gentle shaking. The membrane was reacted in phosphate buffered saline containing 10% Block Ace, 0.1% Tween 20 and 200 ng/ml of anti-heme oxygenase 1 antibody (N-19; Santa Cruz, sc-7696) at room temperature for 1 hour with gentle shaking, and then washed three times in phosphate buffered saline containing 0.1% Tween 20 for 15 minutes with gentle shaking. The membrane was reacted in phosphate buffered saline containing 10% Block Ace, 0.1% Tween 20 and 0.1% peroxidase-labeled rabbit anti-goat IgG (H+L) antibody (Zymed, 61-1620) at room temperature for 1 hour with gentle shaking, and then washed five times in phosphate buffered saline containing 0.1% Tween 20 for 15 minutes with gentle shaking. The PVDF membrane was stained using Western Blot Chemiluminescence Reagent Plus (a product of NEN Life Science Products sold by Daiichi Pure Chemicals, NEL103) according to the attached protocol and exposed to an X-ray film (Kodak, CAT165 1454). After exposure, the film was developed using FPM800 (Fuji Film).

As a result, a band for heme oxygenase 1 protein was observed for each cell to which one of the samples was added. The intensity of the band depended on the concentration of the sample. The results are shown in Table 4. In the table, the intensity of the band for heme oxygenase 1 protein is expressed by the mark +. Specifically, − represents no band observed, and increase in the intensity of the band is represented as follows: +−<+<++.

TABLE 4

| Sample | Intensity of band for heme oxygenase 1 protein |
|---|---|
| Water (negative control) | − |
| Compound (11) at final concentration of 100 μM | + + |
| Compound (11) at final concentration of 50 μM | + |
| Compound (14) at final concentration of 100 μM | + + |
| Compound (14) at final concentration of 50 μM | + |
| Compound (7) at final concentration of 50 μM | + |
| Compound (7) at final concentration of 25 μM | + |
| Compound (17) at final concentration of 100 μM | + + |
| Compound (17) at final concentration of 50 μM | + |
| 15-deoxy-Δ12,14 prostaglandin J₂ (positive control) | + |

INDUSTRIAL APPLICABILITY

The present invention provides a compound of general formula I which is useful as an active ingredient of a composition for inducing apoptosis, a carcinostatic composition, antioxidant compositions such as a composition for inhibiting active oxygen production, a composition for inhibiting lipid peroxide radical production and a composition for inhibiting NO production, an antimicrobial composition to pathogenic microorganism, a composition for preserving freshness, an antimutagenic composition, an anti-hyperglycemic composition or an anti-hyperlipidemic composition, as well as a pharmaceutical composition containing the compound as an active ingredient for treating or preventing a disease sensitive to the compound.

The compound is useful as an active ingredient of a pharmaceutical composition for inducing apoptosis, a carcinostatic pharmaceutical composition, antioxidant pharmaceutical compositions such as a pharmaceutical composition for inhibiting active oxygen production and a pharmaceutical composition for inhibiting NO production, an antimicrobial pharmaceutical composition to pathogenic microorganism, an anti-hyperglycemic pharmaceutical composition or an anti-hyperlipidemic pharmaceutical composition. Furthermore, a food or a drink which contains, which is produced by diluting, and/or which is produced by adding thereto the compound is useful as a functional food or a functional drink having an apoptosis-inducing activity, a carcinostatic activity, antioxidant activities such as an activity of inhibiting active oxygen production and an activity of inhibiting NO production, an antimicrobial activity to pathogenic microorganism, an antimutagenic activity, an anti-hyperglycemic activity or an anti-obese activity. Thus, a food or drink effective in inducing apoptosis in cells in lesions in a patient with cancer or a viral disease to ameliorate the disease states of or preventing such a disease is provided. Apoptosis can be induced in tumor cells upon oral intake of the above-mentioned compounds of the present invention in foods or drinks. Therefore, in case of cancers of digestive organs such as colon cancer and stomach cancer, among others, the foods or drinks of the present invention have excellent effects of preventing or ameliorating the disease state of cancers of digestive organs. Furthermore, the above-mentioned foods or drinks are excellent as anti-oxidative stress foods or drinks based on their antioxidant activities such as the activity of inhibiting the active oxygen production. Furthermore, the present invention provides a sweetener containing the compound of general formula I. It is useful as a low-calorie sweetener in fields of foods and drinks.

In addition, the compounds of general formula I is converted into a compound of general formula IV in vivo, and is particularly useful for constructing a tissue-specific drug delivery system for the compound of general formula IV.

What is claimed is:

1. A compound of general formula I:

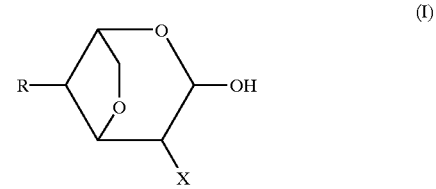

(I)

wherein X is OH or OSO₃H, R is a substituent other than OH, the substituent being a substituent of which the elimination enables introduction of unsaturated bonds at 3-position and 4-position of 3,6-anhydrogalactose or a sulfated derivative thereof and/or a substituent having a tissue-specific affinity.

2. A food or a drink which contains, which is produced by diluting, and/or which is produced by adding thereto the compound of general formula I.

3. The compound according to claim 1, which is selected from the group consisting of 4-O-benzoyl-3,6-anhydro-D-galactose, (4-O-(β-D-2,3,4,6-tetra-O-acetylgalactopyranosyl)-3,6-anhydro-D-galactose, 4-O-(β-D-glucopyranosyl)-3,6-anhydro-D-galactose, 4-O-β-maltotriosyl-3,6-anhydro-D-galactose, 4-O-benzyl-3,6-anhydro-D-galactose, 4-O-acetyl-3,6-anhydro-D-galactose, and 4-O-pentyl-3,6-anhydro-D-galactose.

4. The food or drink of claim 2, wherein the compound of general formula I is selected from the group consisting of 4-O-benzoyl-3,6 anhydro-D-galactose, (4-O-(β-D-2,3,4,6-tetra-O-acetylgalactopyranosyl)-3,6-anhydro-D-galactose, 4-O(β-D-glucopyranosyl)-3,6-anhydro-D-galactose, 4-O-β-maltotriosyl-3,6-anhydro-D-galactose, 4-O-benzyl-3,6-anhydro-D-galactose, 4-O-acetyl-3,6-anhydro-D-galactose, and 4-O-pentyl-3,6-anhydro-D-galactose.

5. A composition, comprising the compound of claim 1 and a pharmaceutically acceptable carrier.

6. A pharmaceutical composition, comprising the compound of general formula I as an active ingredient and a pharmaceutically acceptable carrier, wherein said pharmaceutical composition is selected from the group consisting of a composition for inducing apoptosis, a composition for inhibiting active oxygen production, a composition for inhibiting lipid peroxide radical production, a composition for inhibiting nitrogen monoxide production, a composition for inhibiting prostaglandin E2 synthesis, a composition for regulating cytokine production, a composition for inducing heme oxygenase production, and a composition for immunoregulation.

7. A method for inducing apoptosis, inhibiting active oxygen production, inhibiting lipid peroxide radical production, inhibiting nitrogen monoxide production, inhibiting prostaglandin E2 synthesis, regulating cytokine production, inducing heme oxygenase production, or immunoregulation, comprising administering the pharmaceutical composition of claim 6 to a patient in need thereof.

8. The pharmaceutical composition according to claim 6, which is pharmaceutical composition for treating or inhibiting a disease selected from the group consisting of a systemic lupus erythematosus, immune-mediated glomerulonephritis, multiple sclerosis, collagen disease, rheumatism, inflammatory disease, diabetes, cancer, arteriosclerosis, neurological disease, ischemic re-perfusion disorder, reduction in blood pressure response, vascular dysfunction, antgiectasis cased by diseases, tissue injury, cardiovascular ischemia, hyperalgesia, cerebral ischemia, disease accompanying vascularization, rheumatoid arthritis, osteoarthrosis, goulty arthritis, Behcet's disease, Castleman syndrome, atrial myxoma, multiple myeloma, primary glomerulonephritis, and autoimmune disease.

9. A method for treating or inhibiting a disease selected from the group consisting of a systemic lupus erythematosus, immune-mediated glomerulonephritis, multiple sclerosis, collagen disease, rheumatism, inflammatory disease, diabetes, cancer, arteriosclerosis, neurological disease, ischemic re-perfusion disorder, reduction in blood pressure response, vascular dysfunction, antgiectasis cased by diseases, tissue injury, cardiovascular ischemia, hyperalgesia, cerebral ischemia, disease accompanying vascularization, rheumatoid arthritis, osteoarthrosis, goulty arthritis, Behcet's disease, Castleman syndrome, atrial myxoma, multiple myeloma, primary glomerulonephritis, and autoimmune disease, comprising administering the pharmaceutical composition of claim 8 to a patient in need thereof.

* * * * *